United States Patent
Ha et al.

(10) Patent No.: US 10,143,578 B2
(45) Date of Patent: Dec. 4, 2018

(54) JOINT PROTECTION APPARATUS AND CONTROL METHOD THEREOF

(71) Applicant: Samsung Electronics Co., Ltd., Suwon-Si, Gyeonggi-Do (KR)

(72) Inventors: Tae Sin Ha, Seongnam-si (KR); Young-do Kwon, Yongin-si (KR); Youn Baek Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 463 days.

(21) Appl. No.: 14/498,288

(22) Filed: Sep. 26, 2014

(65) Prior Publication Data

US 2015/0141889 A1    May 21, 2015

(30) Foreign Application Priority Data

Nov. 15, 2013 (KR) .................. 10-2013-0139194

(51) Int. Cl.
*A61F 5/01* (2006.01)

(52) U.S. Cl.
CPC .... *A61F 5/0102* (2013.01); *A61F 2250/0003* (2013.01)

(58) Field of Classification Search
CPC ...... A61H 1/02; A61H 1/0274; A61H 1/0281; A61H 1/0259; A61H 1/0255; A61F 5/0123; A61F 5/0125; A61F 2005/0139; A61F 5/0102; A61F 2005/0167
See application file for complete search history.

(56) References Cited

U.S. PATENT DOCUMENTS

| 7,396,337 B2 * | 7/2008 | McBean ............ A61B 5/04888 601/24 |
| 8,181,520 B2 * | 5/2012 | Kadota ................ A61B 5/1071 601/33 |
| 2006/0128538 A1 | 6/2006 | Sato et al. |

FOREIGN PATENT DOCUMENTS

| JP | 2003220102 A | 8/2003 |
| JP | 2013070785 A | 4/2013 |
| KR | 20100089013 A | 8/2010 |
| KR | 20130073164 A | 7/2013 |

* cited by examiner

*Primary Examiner* — Ophelia A Hawthorne
(74) *Attorney, Agent, or Firm* — Harness, Dickey & Pierce, P.L.C.

(57) ABSTRACT

Disclosed are a joint protection apparatus and a control method thereof. The joint protection apparatus includes a support unit, to which different support frames are coupled via a hinge, a fastening adjustment unit coupled to the support unit to provide fastening force required to fasten the support unit to a human body, a sensing unit configured to sense motion of the different support frames, and a controller configured to decide a motion region in which the motion sensed by the sensing unit is included and to decide the fastening force of the decided motion region.

16 Claims, 16 Drawing Sheets

JOINT PROTECTION APPARATUS AND CONTROL METHOD THEREOF

CROSS-REFERENCE TO RELATED APPLICATION

This application claims the benefit of Korean Patent Applications No. 2013-0139194, filed on Nov. 15, 2013 in the Korean Intellectual Property Office, the disclosure of which is incorporated herein by reference.

BACKGROUND

1. Field

Example embodiments relate to a joint protection apparatus which may be attached to the wearer's body to relieve shock transmitted to the wearer's joint and a control method of the joint protection apparatus.

2. Description of the Related Art

Research and development of human body assistance apparatuses are actively being conducted. Human body assistance apparatuses are used for various purposes including military, industry, rehabilitation, welfare, etc.

Body assistance apparatuses may include joint protection apparatuses, which may be used for physical therapy or rehabilitation training. The joint protection apparatus may refer to an apparatus that relieves shock transmitted to joints to assist people who have difficulty in walking for various reasons, such as damage to cartilages around joints, shortage of muscles around joints, etc. These aforementioned difficulties in walking may be due to innate reasons, such as genetic defects, or acquired reasons, such as diseases, accidents, etc.

In addition, as the average lifespan of humans increases, joint protection apparatuses are increasingly being used for prevention of diseases due to aging, such as osteoporosis and arthritis, as well as physical therapy or rehabilitation.

SUMMARY

Some example embodiments relate to a joint protection apparatus which measures motion of a wearer to adjust fastening force required to fasten the joint protection apparatus to a human body, and a control method of the joint protection apparatus.

Example embodiments will be set forth in part in the description which follows and, in part, will be obvious from the description, or may be learned by practice thereof.

In some example embodiments, the joint protection apparatus may include a support device, the support device including support frames coupled thereto via a hinge; a fastener on the support device, the fastener configured to apply a fastening force to the support device to fasten the support device to a wearer of the joint protection apparatus; sensors configured to sense motions of the support frames; and a controller configured to classify the sensed motions within one of a plurality of motion regions, and to determine the fastening force based on the classified motion region.

In some example embodiments, the controller is configured to determine the fastening force based on a weight of the wearer of the joint protection apparatus and a weight of the joint protection apparatus.

In some example embodiments, the fastening force decided by the controller varies in each of the plurality of motion regions.

In some example embodiments, the sensors are configured to measure an angle of the hinge, and the controller is configured to classify the sensed motion within one of the plurality of motion regions based on the angle.

In some example embodiments, the fastener is configured to apply the fastening force to the support device to fasten the support device to at least one of a hip, knee, ankle, shoulder, elbow, wrist, and waist of the wearer of the joint protection apparatus.

In some example embodiments, the sensors include one or more of an inertial sensor and an electromyography sensor.

In some example embodiments, the sensor configured to measure the angle of the hinge includes at least one of a potentiometer, an absolute encoder, and an incremental encoder.

In some example embodiments, the fastener includes a belt and a motor.

In some example embodiments, the fastener includes an air chamber and an actuator.

In some example embodiments, the controller is configured to determine an assistance torque for the hinge based on the sensed motion, and the joint protection apparatus further includes a driver configured to provide the support unit with the assistance torque.

Some example embodiments relate to a control method of a joint protection apparatus.

In some example embodiments, the method includes sensing motions of support frames coupled to each other via a hinge; classifying the sensed motions within one of a plurality of motion regions; determining a fastening force to apply to the support device based on the classified motion region; and applying, via fasteners on the support frames, the fastening force to a wearer of the joint protection apparatus.

In some example embodiments, determining a fastening force includes determining the fastening force based on a weight of the wearer and a weight of the joint protection apparatus.

In some example embodiments, in each of the plurality of motion regions, the fastening force has a fixed value associated therewith.

In some example embodiments, sensing motions includes measuring an angle of the hinge, and classifying the sensed motions includes classifying the sensed motion within one of the plurality of motion regions based on the angle.

In some example embodiments, applying the fastening force includes applying the fastening force to fasten the support frames on at least one of the hip, knee, ankle, shoulder, elbow, wrist, and waist of the wearer of the joint protection apparatus.

In some example embodiments, sensing motions includes sensing the motions using one of an inertial sensor and an electromyography sensor.

In some example embodiments, sensing motions includes measuring an angle of the hinge using one of a potentiometer, an absolute encoder, and an incremental encoder.

In some example embodiments, the fasteners include a belt and a motor.

In some example embodiments, the fasteners include an air chamber and an actuator.

In some example embodiments, the method further includes determining an assistance torque for the hinge based on the sensed motion; and providing the support frames with the assistance torque using a driver.

BRIEF DESCRIPTION OF THE DRAWINGS

Example embodiments will become apparent and more readily appreciated from the following description of some of the example embodiments, taken in conjunction with the accompanying drawings of which.

DETAILED DESCRIPTION

Figure 1A:
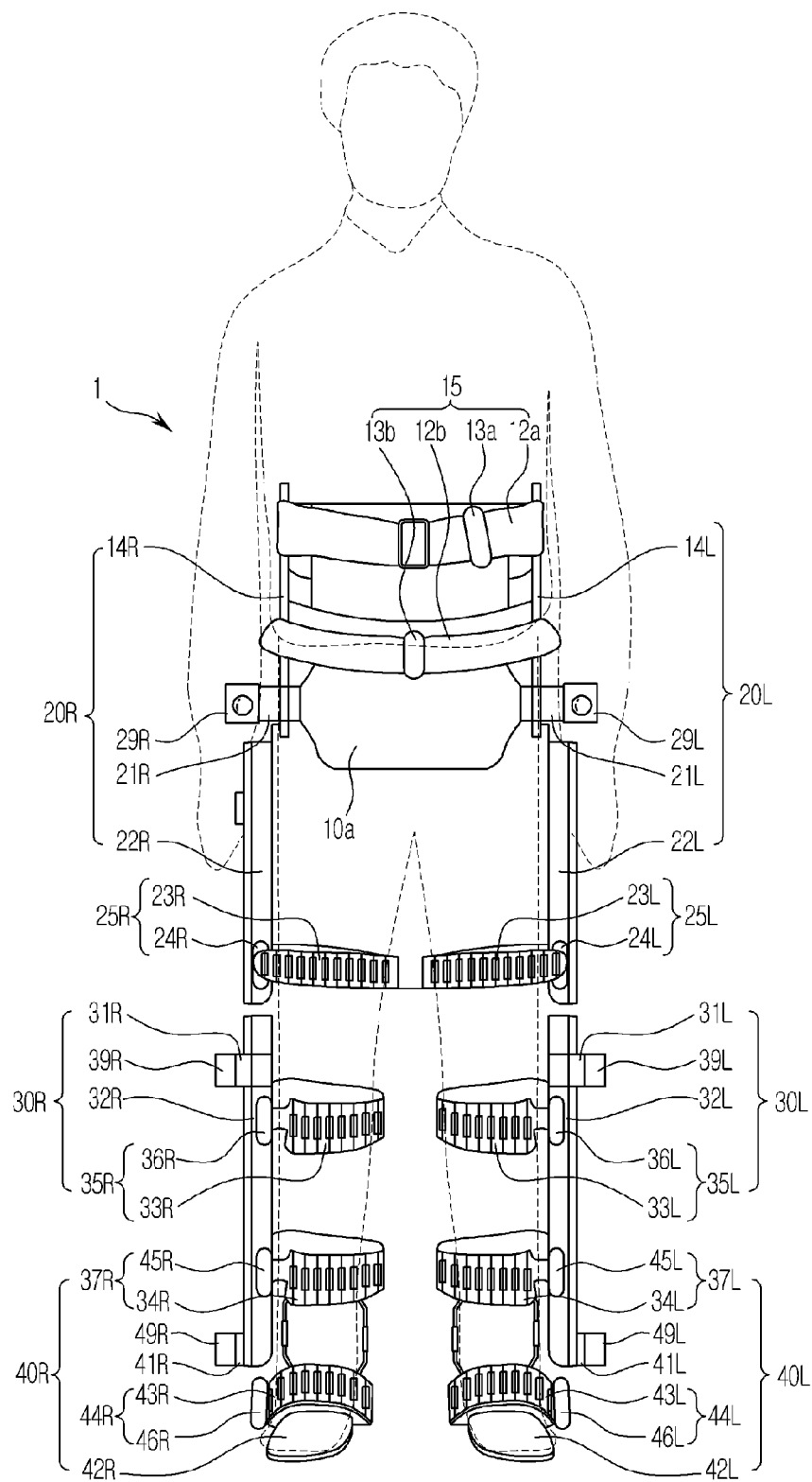
FIG. 1A is a front view of a joint protection apparatus for a lower body according to some example embodiments.

Reference will now be made in detail to example embodiments, some examples of which are illustrated in the accompanying drawings, to allow those skilled in the art to easily understand and reproduce the example embodiments. In the following description of some of the example embodiments, a detailed description of known functions or configurations incorporated herein will be omitted when it may make the subject matter of the disclosure rather unclear.

The terms used in the following description are selected by taking into consideration the functions obtained in accordance with the embodiments, and these terms may be replaced by other terms based on intensions of those skilled in the art, customs, or the like. Hence, the meanings of terms used in the following description of the embodiments must follow definitions concretely described in the specification, and must be construed as having a general meaning typically recognized by those skilled in the art so long as there are no concrete definitions.

In addition, even if selectively described configurations of the example embodiments are shown as a single integrated configuration in the drawings, so long as there is no additional explanation, it should be understood that they may be freely combined with one another if those skilled in the art judge that the combinations have no clear technical contradictions.

Hereinafter, some example embodiments of a joint protection apparatus will be described with reference to the accompanying drawings.

Figure 1B:
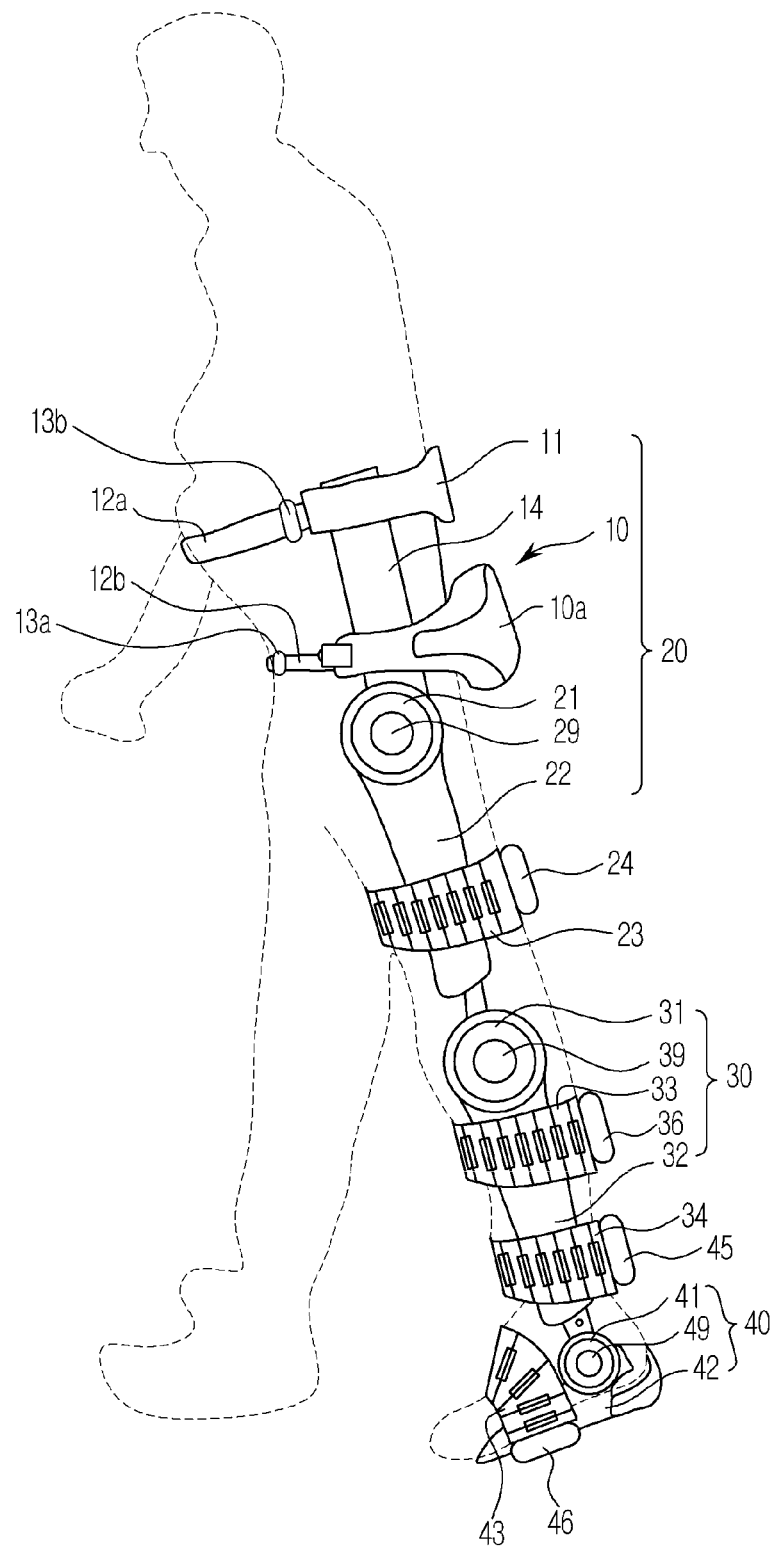
FIG. 1B is a side view of the joint protection apparatus for the lower body according to some example embodiments.
Figure 1C:
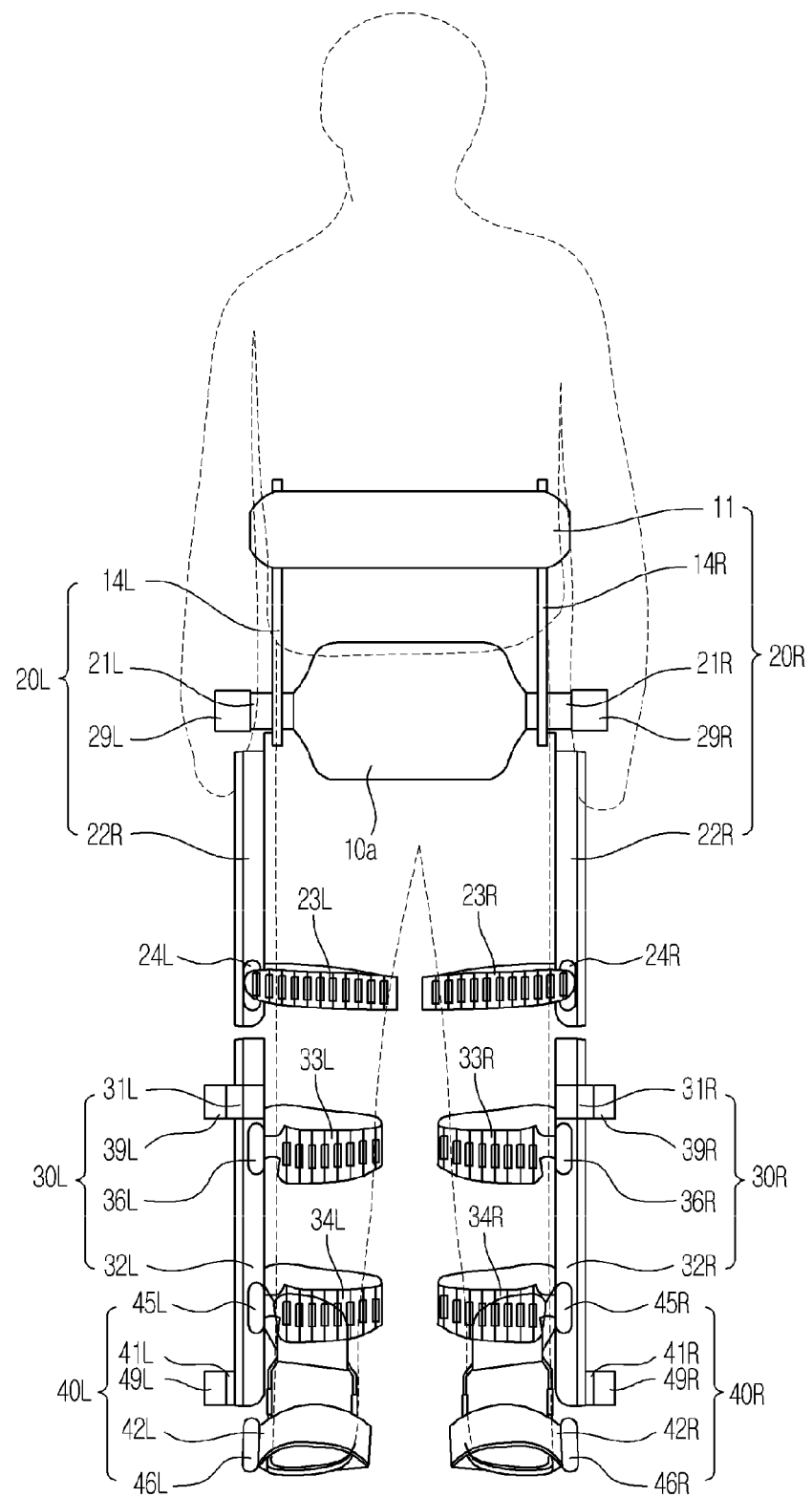
FIG. 1C is a rear view of the joint protection apparatus for the lower body according to some example embodiments.

FIGS. 1A, 1B, and 1C are respectively a front view, a side view, and a rear view of a joint protection apparatus according to some example embodiments.

Referring to FIGS. 1A, 1B, and 1C, the joint protection apparatus 1 may include a housing 10a and joint protectors 20, 30, 40.

The housing 10a may function to protect a variety of elements mounted therein and to stably fix the variety of elements. The housing 10a may contain various processors, such as a Central Processing Unit (CPU) and/or a Graphic Processing Unit (GPU), which correspond to a controller, and a printed circuit board. In addition, the housing 10a may contain various kinds of storage devices as needed.

The Central Processing Unit (CPU) mounted in the housing 10a may be a microprocessor. The microprocessor is a processing device in which an arithmetic logic unit, a register, a program counter, an instruction decoder, a control circuit, or the like is mounted on at least one silicon chip. The central processing unit may generate control signals to control operation of the joint protectors 20, 30, 40 and transmit the generated control signals to the joint protectors 20, 30, 40. According to some example embodiments, the central processing unit may measure motion of a support frame during walking of a wearer, and implement signal processing for division of the measured motion into two or more motion regions and signal processing for decision of assistance torques corresponding to the divided motion regions.

For example, the controller may include a processor and a memory (not shown).

Figure 10:
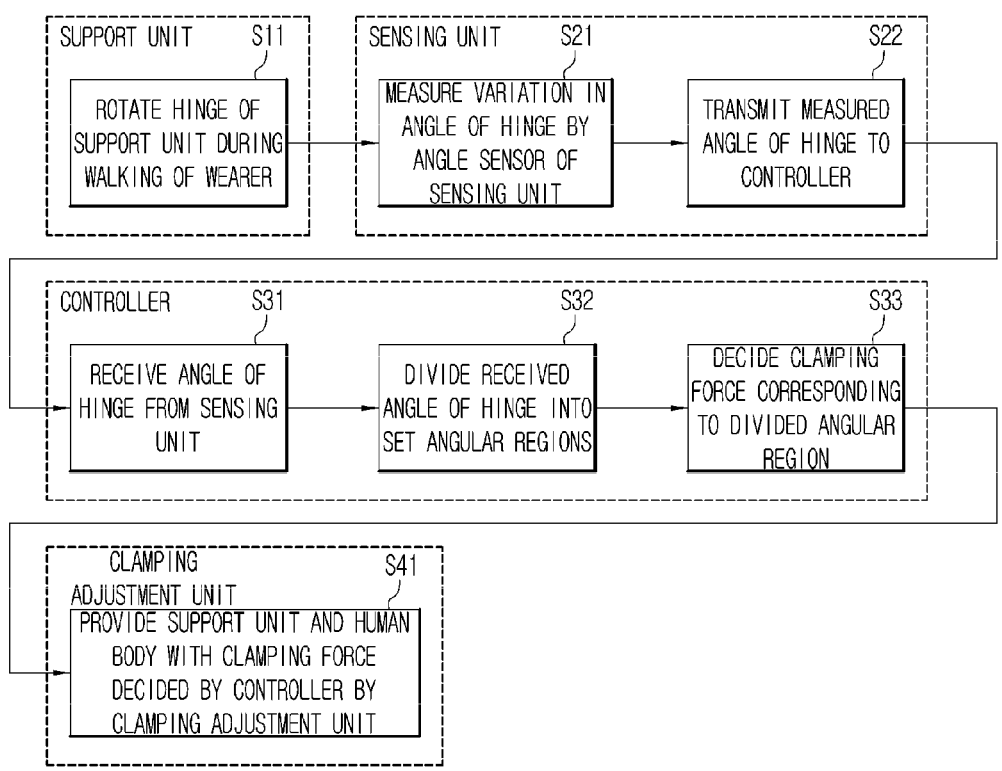
FIG. 10 is a block diagram showing decision and provision of fastening force by a support unit, a sensing unit, a controller, and a fastening adjustment unit according to some example embodiments.
Figure 11:
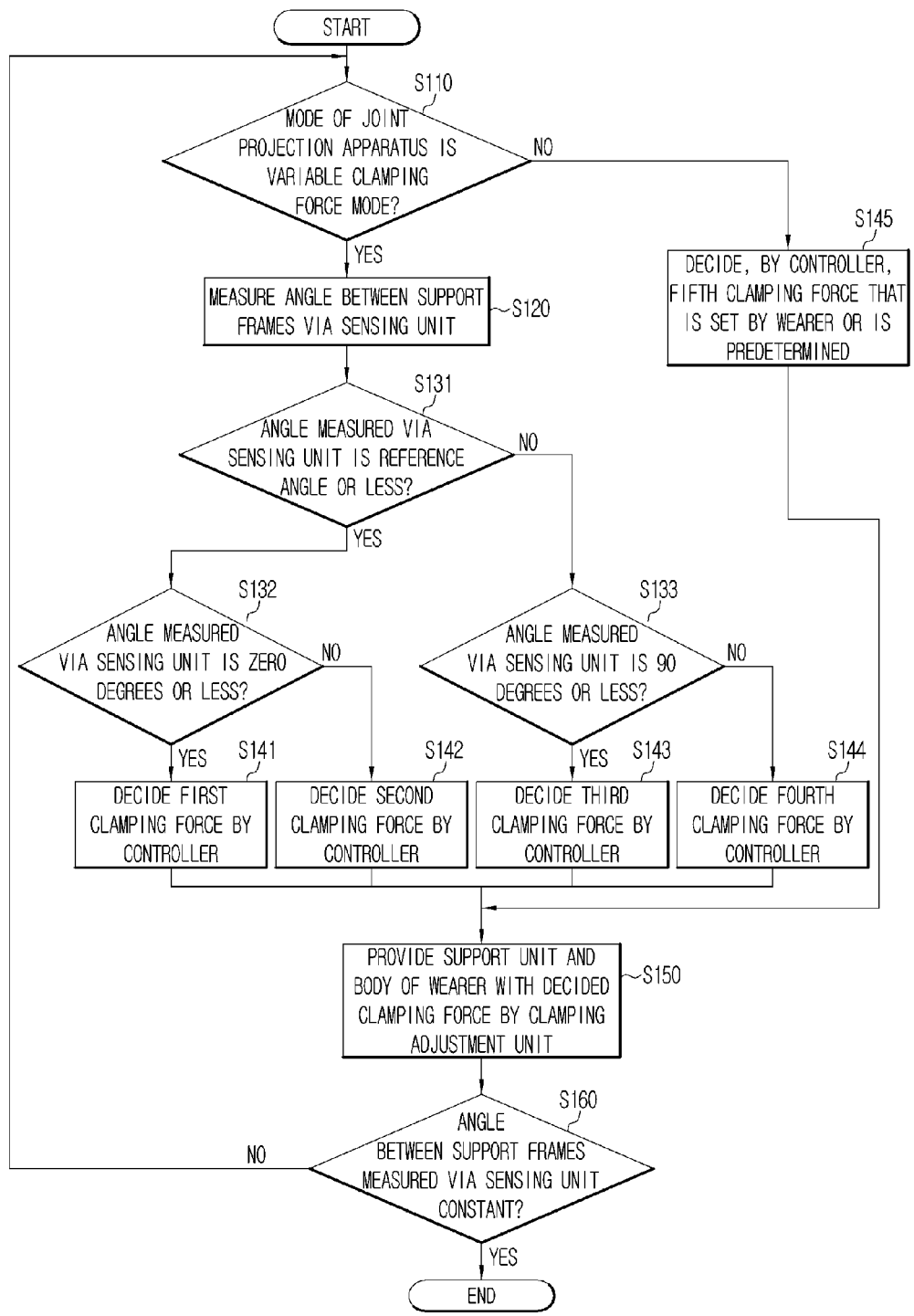
FIG. 11 is a flowchart showing a process of measuring the angle of a hinge by a sensing unit, dividing the measured angle into four angular regions, and providing a support unit with fastening force corresponding to each angular region.

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processing device as a special purpose computer to perform the operations illustrated in FIGS. 10 and 11, such that the controller controls fasteners 15, 25, 35, 37, 44, 54, 57, 64, and/or 67 to apply corresponding fastening forces to a wearer of the joint protection apparatus 1 based on one or more of an angle of a hinge of support frames to which the fasteners are coupled, a weight of the wearer and a weight of the joint protection apparatus 1. Moreover, the controller may be programmed to utilize different equations to determine the fastening force based on the aforementioned angle of the hinge.

The Graphic Processing Unit (GPU) is a processing device, such as a microprocessor, which processes graphic information. The graphic processing unit may assist a graphic processing function of the central processing unit or may implement graphic processing alone. According to some example embodiments, the graphic processing unit may implement signal processing for display of current motion of a support frame, a corresponding region of the current motion, currently provided fastening force, the angle of a hinge, the gradient of a support frame, walking speed, assistance torque applied to a hinge, and electromyography (EMG) patterns.

The printed circuit board is a board on which a circuit is printed. The central processing unit, the graphic processing unit, and various kinds of storage devices may be mounted on the printed circuit board. According to some example embodiments, the printed circuit board may be attached to an inner surface of the housing 10a and function to stably fix positions of the CPU and the like to the housing 10a.

The housing 10a may contain various kinds of storage devices, for example, non-transitory computer readable media. The instructions executed by the processor may be stored on the non-transitory computer readable medium. Examples of non-transitory computer-readable medium include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable medium may also be a distributed network, so that the program instructions are stored and executed in a distributed fashion.

Examples of the storage devices may include a magnetic disc storage device that stores data in a magnetized disc surface, and a semiconductor memory device that stores data using various kinds of semiconductor memories. The storage device may store currently measured motion, two or more motion regions, EMG patterns, assistance torque applied to a hinge, etc.

The housing 10a may further contain a power source to supply power to various inner elements of the housing 10a or the joint protectors 20, 30, 40.

In addition, an actuator to control operation of the joint protectors 20, 30, 40 or to drive the joint protectors 20, 30, 40 may further be mounted in the housing 10a.

The joint protectors 20, 30, 40 may include a support unit that receives shock to be applied to joints of the wearer and relieve the shock. The support unit may include hinges, first support frames, and second support frames, for example.

The joint protection apparatus 1 may include a plurality of fastening adjustment units to fix the joint protection apparatus 1 to a wearer. The fastening adjustment units may include a fixing member and a fixing member fastener.

For example, to fasten the housing 10a or a waist support member 11 to the wearer, the joint protector 20 may include at least one waist fastening adjustment unit 15. The waist fastening adjustment unit 15 may include waist fixing members 12a, 12b and waist fixing member fasteners 13a, 13b.

Various members, which may fix the housing 10a to the waist or the hips, may be used as the waist fixing members 12a, 12b. For example, the waist fixing members 12a, 12b may be elastic belts, various kinds of straps, or bands having an air chamber.

The waist fixing member fasteners 13a, 13b may be coupled to the waist fixing members 12a, 12b to provide the waist fixing members 12a, 12b with fastening force. Various fasteners, which may tighten the waist fixing members 12a, 12b to provide the waist of the wearer, first hip support frames 14R, 14L, and second hip support frames 22R, 22L with fastening force, may be used as the waist fixing member fasteners 13a, 13b. For example, the waist fixing member fasteners 13a and 13b may include a belt and a motor, or may include an air chamber and an actuator.

According to some example embodiments, joint motion sensing units 29, 39, 49 may measure the angle of a joint, walking speed, the angular velocity of a joint, the attitude of the wearer, electrical signals with regard to muscles, etc. The angle of a joint may be represented as the angle of a hinge used to couple different support frames to each other.

In some example embodiments, the joint motion sensing units 29, 39, 49 may be located at hinges coupling first and second support frames to each other, or may be located at assistance torque provision units 21, 31, 41 that apply assistance torque to the support frames and the hinges.

The joint motion sensing units 29, 39, 49 may measure the angle of a joint using an angle sensor, such as a potentiometer, an absolute encoder, or an incremental encoder. A potentiometer is an angle sensor that calculates an electrical input directly proportional to the movement angle of a joint via variation of resistance depending on angle. An absolute encoder is an angle sensor that detects a rotation angle at a corresponding position using optical pulse waves without setting a reference position. An incremental encoder is an angle sensor that detects a rotation angle at a corresponding position using optical pulse waves by calculating a rate of change on the basis of a reference position.

To measure the angle of a joint using the potentiometer, an analog-to-digital conversion process may be implemented on the analog output signal of the potentiometer. The potentiometer may measure an angle by noise filtering an output signal thereof using a Low Pass Filter (LPF), and thereafter converting the noise removed analog signal into a digital signal.

To measure the angle of a joint using the encoder, a digital signal output from the encoder is noise filtered. However, analog to digital conversion may be unnecessary. The encoder may measure an angle by converting optical pulse waves into a digital electrical signal and pulse counting the digital signal.

In addition, the joint motion sensing units 29, 39, 49 may include at least one Inertial Measurement Unit (IMU). The inertial measurement unit may include at least one of a multi-axis inertial sensor, such as a tri-axis inertial sensor, and a gyro sensor. According to some example embodiments, the inertial measurement unit may measure the attitude of the wearer, or may calculate walking speed via measurement of walking acceleration.

The joint motion sensing units 29, 39, 49 may further include at least one electromyography (EMG) system. Electromyography is a method of measuring movement of muscles by sensing electrical variation in the muscles based on muscular reaction to neural stimulation using an electromyography system. Accordingly, in some example embodiments, movement patterns of muscles of the wearer may be divided via electromyography measurement, and analytic results of the divided patterns may be utilized to increase fastening force when a relatively large shock is transmitted to the wearer's joint.

The joint protectors 20, 30, 40, as shown in FIGS. 1A, 1B, and 1C, may include a hip joint protector 20, a knee joint protector 30, and an ankle joint protector 40.

The hip joint protector 20 may relieve shock to be transmitted to the upper leg and the hip joint of the wearer during walking. The knee joint protector 30 may relieve shock to be transmitted to the lower leg and the knee joint of the wearer during walking. The ankle joint protector 40 may relieve shock to be transmitted to the ankle joint of the wearer during walking.

In some example embodiments, the joint protection apparatus 1 may selectively include the hip joint protector 20, the knee joint protector 30, and the ankle joint protector 40. Accordingly, the hip joint protector 20, the knee joint protector 30, and/or the ankle joint protector 40 may be worn by the wearer on at least one of the hip, the knee, and the ankle of the wearer.

In other example embodiments, the hip joint protector 20, the knee joint protector 30, and/or the ankle joint protector 40 may be worn by the wearer at any one of the left leg and the right leg of the wearer.

In other example embodiments, the hip joint protector 20, the knee joint protector 30, and/or the ankle joint protector 40 may include a pair of hip joint protectors 20R, 20L, a pair of knee joint protectors 30R, 30L, and/or a pair of ankle joint protectors 40R, 40L, which may be worn by the wearer at the right leg and the left leg to assist bipedal walking.

Hereinafter, for convenience of explanation, the joint protection apparatus 1 including plural hip joint protectors 20R, 20L, plural knee joint protectors 30R, 30L, and plural ankle joint protectors 40R, 40L will be described. However, as discussed above, example embodiments are not limited thereto.

The plural hip joint protectors 20R, 20L may include the first hip support frames 14R, 14L, the second hip support frames 22R, 22L, the waist fastening adjustment unit 15 including the waist fixing members 12a, 12b and the waist fixing member fasteners 13a, 13b, thigh fastening adjustment units 25R, 25L including thigh fixing members 23R, 23L and thigh fixing member fasteners 24R, 24L, hip joint assistance torque provision units 21R, 21L, and hip joint motion sensing units 29R, 29L.

As shown in FIGS. 1A, 1B, and 1C, one or more first hip support frames 14R, 14L and one or more second hip support frames 22R, 22L may be provided. The first hip support frames 14R, 14L and the second hip support frames 22R, 22L may have various shapes as needed. For example, the first hip support frames 14R, 14L and the second hip support frames 22R, 22L may have a hexahedral shape, or may be a combination of plural support bars.

The first hip support frames 14R, 14L and the second hip support frames 22R, 22L may be constructed by connecting a plurality of links to one another. A plurality of hinges may be interposed between the plurality of links to connect the links to one another. The plurality of hinges may be rotatable in at least one direction. As such, the first hip support frames 14R, 14L and the second hip support frames 22R, 22L may bend in at least one direction within a prescribed range based on a rotation range of the plurality of hinges. According to some example embodiments, a single hinge or a plurality of hinges may be connected to two links among a plurality of links. If a plurality of hinges is connected to two links, the respective hinges may be rotatable in different directions. As such, the first hip support frames 14R, 14L and the second hip support frames 22R, 22L may bend in various directions within a prescribed range.

According to some example embodiments, the first hip support frames 14R, 14L and the second hip support frames 22R, 22L may be formed of flexible materials, and may bend within a range based on flexibility of materials.

The plural hip joint protectors 20R, 20L may include the waist fixing members 12a, 12b and the thigh fixing members 23R, 23L to fix the first hip support frames 14R, 14L and the second hip support frames 22R, 22L to the hip joints and the upper legs of the wearer. That is, the first hip support frames 14R, 14L and the second hip support frames 22R, 22L may be fixed to the inner side or outer side of the hip joints and the upper legs of the wearer via the waist fixing members 12a, 12b and the thigh fixing members 23R, 23L. When the first hip support frames 14R, 14L and the second hip support frames 22R, 22L are rotated by walking torque applied by muscles of the wearer or assistance torque provided by the hip joint assistance torque provision units 21R, 21L, the hip joints and the upper legs fixed to the first hip support frames 14R, 14L and the second hip support frames 22R, 22L may be rotated in the same direction about the hip joints.

The waist fastening adjustment unit 15 and the thigh fastening adjustment units 25R, 25L may respectively function to provide fastening force required to fasten a support unit including support frames to the waist and the thighs. The waist fastening adjustment unit 15 may include the waist fixing members 12a, 12b and the waist fixing member fasteners 13a, 13b. The thigh fastening adjustment units 25R, 25L may include the thigh fixing members 23R, 23L and the thigh fixing member fasteners 24R, 24L.

The waist fixing members 12a, 12b and the thigh fixing members 23R, 23L may be formed of metal, or may be formed of various elastic materials, such as rubber, etc. For example, the waist fixing members 12a, 12b and the thigh fixing members 23R, 23L may be elastic belts or various kinds of straps, or may include an air chamber and a belt including an inner shell and an outer shell surrounding the air chamber. In other examples, various other fixing members to fix the first hip support frames 14R, 14L and the second hip support frames 22R, 22L to the upper legs may serve as the waist fixing members 12a, 12b and the thigh fixing members 23R, 23L.

As the waist fixing members 12a, 12b and the thigh fixing members 23R, 23L are fixed to the hip joints and the upper legs, the hip joint protectors 20R, 20L may apply a desired (e.g., a prescribed) assistance torque to the upper legs or the hip joints of the wearer so as to assist the wearer in raising or lowering the upper legs. As such, the wearer may conveniently raise the legs, or may implement walking motion.

The waist fixing member fasteners 13a, 13b and the thigh fixing member fasteners 24R, 24L may be connected to the waist fixing members 12a, 12b and the thigh fixing members 23R, 23L to provide the waist and the thighs of the wearer, the first hip support frames 14R, 14L and the second hip support frames 22R, 22L with fastening force.

In some example embodiments, the waist fixing member fasteners 13a, 13b and the thigh fixing member fasteners 24R, 24L may include a motor and a belt. When strong shock is transmitted to the hip joints, to allow the hip joint protectors 20R, 20L to come into close contact with the hips of the wearer, the belt may be pulled using the motor to transmit pulling force to the waist fixing members 12a, 12b and the thigh fixing members 23R, 23L, which may result in a strong fastening force. Conversely, when strong shock is not transmitted to the hip joints, the motor generates weak pulling force of the belt to enhance wearing convenience of the hip joint protectors 20R, 20L, which may cause the waist fixing members 12a, 12b and the thigh fixing members 23R, 23L to provide the waist and the thighs of the wearer, the first hip support frames 14R, 14L, and the second hip support frames 22R, 22L with weak fastening force.

In other example embodiments, the waist fixing member fasteners 13a, 13b and the thigh fixing member fasteners 24R, 24L may include an air chamber and an actuator. In some example embodiments, the air chamber may be defined in the entire belt. Alternatively, in other example embodiments, the air chamber may be defined in a belt length adjustor connected to an inner belt. In the case in which the air chamber is provided in the entire belt, air is introduced into the air chamber to increase the human body seating area of the waist fixing members 12a, 12b and the thigh fixing members 23R, 23L, which may provide strong fastening force. Then, air of the air chamber may be discharged to reduce the human body seating area of the waist fixing members 12a, 12b and the thigh fixing members 23R, 23L, which may provide weak fastening force.

In the case in which the air chamber is defined in the belt length adjustor connected to the inner belt, the waist fixing member fasteners 13a, 13b and the thigh fixing member fasteners 24R, 24L may introduce air into the air chamber to shorten a length of the air chamber and pull the inner belt. As the pulling force is transmitted to the waist fixing members 12a, 12b and the thigh fixing members 23R, 23L, strong fastening force may be provided. Conversely, as air of the air chamber is discharged to lengthen a length of the air chamber, weak fastening force may be provided.

The hip joint assistance torque provision units 21R, 21L may generate various magnitudes of assistance torque in at least one direction by being rotated in at least one direction, thereby applying the assistance torque to the first hip support frames 14R, 14L and the second hip support frames 22R, 22L. The hip joint assistance torque provision units 21R, 21L may be set to be rotated within a movement range of the hip joints.

In one embodiment, the hip joint assistance torque provision units 21R, 21L may include at least one motor that generates a desired (or, alternatively, a prescribed) magnitude of torque based on electric power supplied from the joint protectors 20, 30, 40. In addition, the hip joint assistance torque provision units 21R, 21L may include at least one piston or cylinder device that is operated by electric power or hydraulic or pneumatic pressure from the joint protectors 20, 30, 40 to generate torque. In addition, according to some example embodiments, the hip joint assistance torque provision units 21R, 21L may include at least one motor as well as at least one piston or cylinder device.

One or more first hip support frames 14R, 14L and one or more second hip support frames 22R, 22L may be physically connected to the hip joint assistance torque provision units 21R, 21L, and may be rotated in at least one direction by assistance torque generated by the hip joint assistance torque provision units 21R, 21L.

The plural knee joint protectors 30R, 30L may include first knee support frames 22R, 22L, second knee support frames 32R, 32L, the thigh fastening adjustment units 25R, 25L including the thigh fixing members 23R, 23L and the thigh fixing member fasteners 24R, 24L, shank fastening adjustment units 35R, 35L including shank fixing members 33R, 33L and shank fixing member fasteners 36R, 36L, knee joint assistance torque provision units 31R, 31L, and knee joint motion sensing units 39R, 39L.

The thigh fastening adjustment units 25R, 25L and the shank fastening adjustment units 35R, 35L may respectively function to provide fastening force required to fasten a support unit including support frames to the thighs and the shanks. The thigh fastening adjustment units 25R, 25L may include the thigh fixing members 23R, 23L and the thigh fixing member fasteners 24R, 24L, and the shank fastening adjustment units 35R, 35L may include the shank fixing members 33R, 33L and the shank fixing member fasteners 36R, 36L.

The second hip support frames 22R, 22L may also function as a first knee support frames 22R, 22L. The first knee support frames 22R, 22L and the second knee support frames 32R, 32L may be fixed to the inner side or outer side of the upper legs and the lower legs of the wearer via the thigh fixing members 23R, 23L and the shank fixing members 33R, 33L. A configuration, structure, and material of the shank fixing members 33R, 33L may equal to or different from those of the waist fixing members 12a, 12b and the thigh fixing members 23R, 23L as described above.

As the upper legs and the lower legs of the wearer may be fixed to the first knee support frames 22R, 22L and the second knee support frames 32R, 32L by the thigh fixing members 23R, 23L and the shank fixing members 33R, 33L, the knee joint protectors 30R, 30L may apply a desired (or, alternatively, a prescribed) magnitude of assistance torque to the lower legs or the knee joints of the wearer. Thereby, the knee joint protectors 30R, 30L may assist the wearer in raising or lowering the lower legs.

In some example embodiments, the thigh fixing member fasteners 24R, 24L and the shank fixing member fasteners 36R, 36L may provide the shank fixing members 23R, 23L, the shank fixing members 33R, 33L, the shank and the thighs of the wearer, the first knee support frames 22R, 22L, and the second knee frames 32R, 32L with fastening force.

When relatively strong shock is applied to the knees, the thigh fixing member fasteners 24R, 24L and the shank fixing member fasteners 36R, 36L cause the knees to come into close contact with the first knee support frames 22R, 22L and the second knee support frames 32R, 32L with strong fastening force, thereby relieving shock to be transmitted to the knees of the wearer by transmitting the shock to the first knee support frames 22R, 22L and the second knee support frames 32R, 32L. When relatively weak shock is applied to the knees, the thigh fixing member fasteners 24R, 24L and the shank fixing member fasteners 36R, 36L may provide weak fastening force to enhance wearing convenience of the joint projectors 30R, 30L at the thighs and the shanks of the wearer.

A configuration, structure, and material of the shank fixing member fasteners 36R, 36L may be equal to or different from the waist fixing member fasteners 13a, 13b and the thigh fixing member fasteners 24R, 24L as described above.

One or more of the first knee support frames 22R, 22L and one or more of the second knee support frames 32R, 32L may be physically connected to the knee joint assistance torque provision units 31R, 31L, and may be rotated in at least one direction by assistance torque generated by the knee joint assistance torque provision units 31R, 31L. A configuration, structure, and material of the first knee support frames 22R, 22L and the second knee support frames 32R, 32L may be equal to or different from those of the first hip support frames 14R, 14L and the second hip support frames 22R, 22L as described above.

The knee joint assistance torque provision units 31R, 31L may generate various magnitudes of assistance torque in at least one direction. The knee joint assistance torque provision units 31R, 31L may be set to be driven within a movement range of the knee joints.

The plural ankle joint protectors 40R, 40L may include first ankle support frames 32R, 32L, second ankle support frames 42R, 42L, ankle fastening adjustment units 37R, 37L including ankle fixing members 34R, 34L and ankle fixing member fasteners 45R, 45L, instep fastening adjustment units 44R, 44L including instep fixing members 43R, 43L and instep fixing member fasteners 46R, 46L, ankle joint assistance torque provision units 41R, 41L, and ankle joint motion sensing units 49R, 49L.

The ankle fastening adjustment units 37R, 37L and the instep fastening adjustment units 44R, 44L may respectively function to provide fastening force required to fasten a support unit including support frames to the ankles and the insteps. The ankle fastening adjustment units 37R, 37L may include the ankle fixing members 34R, 34L and the ankle fixing member fasteners 45R, 45L, and the instep fastening adjustment units 44R, 44L may include the instep fixing members 43R, 43L and the instep fixing member fasteners 46R, 46L.

The ankle fixing members 34R, 34L and the instep fixing members 43R, 43L may be connected to the first ankle support frames 32R, 32L and the second ankle support frames 42R, 42L, and may function to fix the ankles of the wearer to the first ankle support frames 32R, 32L and the second ankle support frames 42R, 42L. A configuration, structure, and material of the ankle fixing members 34R, 34L and the instep fixing members 43R, 43L may be equal to or different from those of the waist fixing members 12a, 12b and the thigh fixing members 23R, 23L as described above.

In some example embodiments, the ankle fixing member fasteners 45R, 45L and the instep fixing member fasteners 46R, 46L may provide the ankle fixing members 34R, 34L, the instep fixing members 43R, 43L, the ankles of the wearer, the first ankle support frames 32R, 32L, and the second ankle support frames 42R, 42L with fastening force.

When relatively strong shock is applied to the ankles, the ankle fixing member fasteners 45R, 45L and the instep fixing member fasteners 46R, 46L may cause the ankles and the insteps of the wearer to come into close contact with the first ankle support frames 32R, 32L and the second ankle support frames 42R, 42L with strong fastening force, thereby relieving shock to be transmitted to the ankles of the wearer by transmitting the shock to the first ankle support frames 32R, 32L and the second ankle support frames 42R, 42L. When relatively weak shock is applied to the ankles, the ankle fixing member fasteners 45R, 45L and the instep fixing member fasteners 46R, 46L may provide weak fastening force to enhance wearing convenience of the joint protectors 40R, 40L at the ankles and the insteps of the wearer.

A configuration, structure, and material of the ankle fixing member fasteners 45R, 45L and the instep fixing member fasteners 46R, 46L may be equal to or different from those of the waist fixing member fasteners 13a, 13b and the thigh fixing member fasteners 24R, 24L as described above.

Soles of the wearer may be seated on the second ankle support frames 42R, 42L.

A pressure sensor may be installed to each of the second ankle support frames 42R, 42L. The pressure sensor may sense the weight of the wearer, thereby sensing whether or not the wearer wears the joint protection apparatus 1 and/or whether or not the wearer stands up.

Each of the second ankle support frames 42R, 42L may be provided with a Ground Reaction Force (GRF) sensor that is a pressure sensor to sense ground reaction force transmitted to the wearer's foot during walking.

In some example embodiments, the ankle joint assistance torque provision units 41R, 41L may include at least one motor or at least one piston or cylinder device that generates a prescribed magnitude of torque based on electric power or hydraulic pressure directly transmitted from the joint protectors 20, 30, 40, or electric power or hydraulic pressure indirectly transmitted through the hip joint protectors 20R, 20L. Similar to the above description, the ankle joint assistance torque provision units 41R, 41L may include at least one motor as well as at least one piston or cylinder device.

According to some example embodiments, the number of the fastening adjustment units 15, 25R, 25L, 35R, 35L, 37R, 37L, 44R, 44L of the joint protection apparatus 1 may be greater or less than the above description based on the designer of the joint protection apparatus 1.

In some example embodiments, driving and operation of the above described joint protectors 20, 30, 40 may be initiated or controlled by an actuator installed to a controller. In addition, the joint protectors 20, 30, 40 may individually receive control signals and individually initiate operation thereof.

Through the above described elements and operation thereof, the joint protection apparatus 1 may assist the wearer in walking.

Hereinafter, respective components of the joint protection apparatus 1 to control joint protectors 50 and 60 of the joint protection apparatus 1 will be described with reference to FIG. 2.

Figure 2:
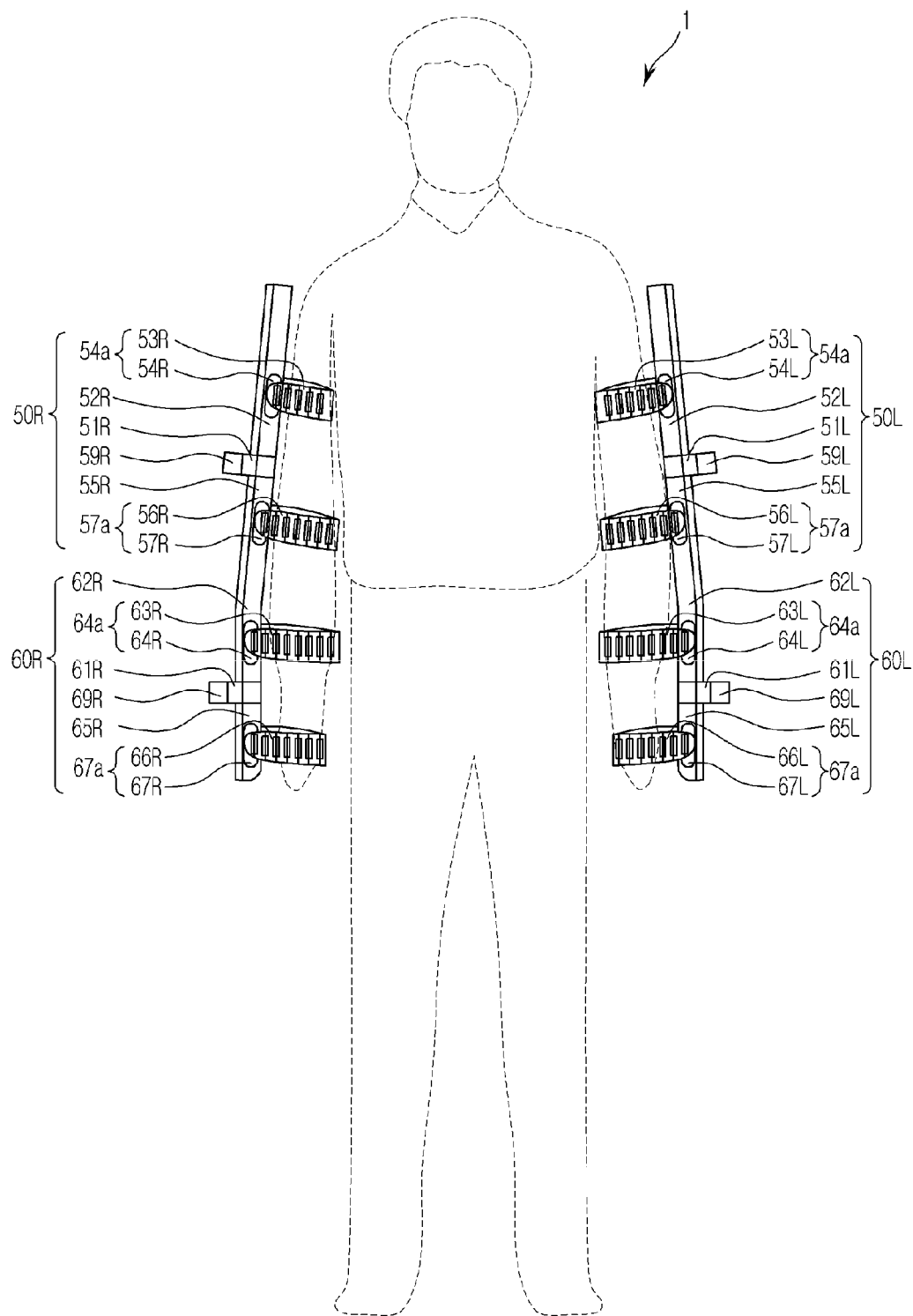
FIG. 2 is a front view of a joint protection apparatus for an upper body according to some example embodiments.

FIG. 2 is a front view of a joint protection apparatus according to some example embodiments.

Referring to FIG. 2, the joint protection apparatus 1 may include joint protectors 50 and 60.

Plural elbow joint protectors 50R, 50L may include first elbow support frames 52R, 52L, second elbow support frames 55R, 55L, an upper arm fastening adjustment unit 54a including upper arm fixing members 53R, 53L and upper arm fixing member fasteners 54R, 54L, a lower arm fastening adjustment unit 57a including lower arm fixing members 56R, 56L and lower arm fixing member fasteners 57R, 57L, elbow joint assistance torque provision units 51R, 51L, and elbow joint motion sensing units 59R, 59L.

The upper arm fastening adjustment unit 54a and the lower arm fastening adjustment unit 57a may respectively function to provide fastening force required to fasten a support unit including support frames to the upper arms and the lower arms. The upper arm fastening adjustment unit 54a may include the upper arm fixing members 53R, 53L and the upper arm fixing member fasteners 54R, 54L, and the lower arm fastening adjustment unit 57a may include the lower arm fixing members 56R, 56L and the lower arm fixing member fasteners 57R, 57L.

The first elbow support frames 52R, 52L and the second elbow support frames 55R, 55L may be fixed to the inner side or outer side of the upper arms and the lower arms of the wearer via the upper arm fixing members 53R, 53L and the lower arm fixing members 56R, 56L. A configuration, structure, and material of the upper arm fixing members 53R, 53L and the lower arm fixing members 56R, 56L may be equal to or different from those of the waist fixing members 12a, 12b and the thigh fixing members 23R, 23L as described above with reference to FIGS. 1A, 1B, and 1C.

As the upper arms and the lower arms may be fixed to the first elbow support frames 52R, 52L and the second elbow support frames 55R, 55L via the upper arm fixing members 53R, 53L and the lower arm fixing members 56R, 56L, the elbow joint protectors 50R, 50L may apply a desired (or, alternatively, a prescribed) magnitude of assistance torque to the upper arms, the lower arms, and the elbow joints of the wearer. As such, the elbow joint protectors 50R, 50L may assist the wearer in raising or lowering the lower arms.

In some example embodiments, the upper arm fixing member fasteners 54R, 54L and the lower arm fixing member fasteners 57R, 57L may provide the upper arm fixing members 53R, 53L, the lower arm fixing members 56R, 56L, the upper arms and the lower arms of the wearer, the first elbow support frames 52R, 52L, and the second elbow support frames 55R, 55L with fastening force.

When relatively strong shock is applied to the elbows, the upper arm fixing member fasteners 54R, 54L and the lower arm fixing member fasteners 57R, 57L may cause the upper arms and the lower arms of the wearer to come into close contact with the first elbow support frames 52R, 52L and the second elbow support frames 55R, 55L with strong fastening force, thereby relieving shock to be transmitted to the elbows of the wearer by transmitting the shock to the first elbow support frames 52R, 52L and the second elbow support frames 55R, 55L. When relatively weak shock is transmitted to the elbows, the upper arm fixing member fasteners 54R, 54L and the lower arm fixing member fasteners 57R, 57L may provide weak fastening force to enhance wearing convenience of the joint protectors 50R, 50L at the upper arms and the lower arms of the wearer.

A configuration, structure, and material of the upper arm fixing member fasteners 54R, 54L and the lower arm fixing member fasteners 57R, 57L may be equal to or different from the waist fixing member fasteners 13a, 13b and the thigh fixing member fasteners 24R, 24L as described above with reference to FIGS. 1A, 1B, and 1C.

One or more of the first elbow support frames 52R, 52L and one or more of the second elbow support frames 55R, 55L may be physically connected to the elbow joint assistance torque provision units 51R, 51L, and may be rotated in at least one direction by assistance torque provided by the elbow joint assistance torque provision units 51R, 51L. A configuration, structure, and material of the first elbow support frames 52R, 52L and the second elbow support frames 55R, 55L may be equal to or different from those of the first hip support frames 14R, 14L and the second hip support frames 22R, 22L as described above with reference to FIGS. 1A, 1B, and 1C.

The elbow joint assistance torque provision units 51R, 51L may generate various magnitudes of assistance torque in at least one direction. The elbow joint assistance torque provision units 51R, 51L may be set to be driven within a movement range of the elbow joints.

Plural wrist joint protectors 60R, 60L may include first wrist support frames 62R, 62L, second wrist support frames 65R, 65L, a wrist fastening adjustment unit 64a including wrist fixing members 63R, 63L and wrist fixing member fasteners 64R, 64L, a backhand fastening adjustment unit 67a including backhand fixing members 66R, 66L and backhand fixing member fasteners 67R, 67L, wrist joint assistance torque provision units 61R, 61L, and wrist joint motion sensing units 69R, 69L.

The wrist fastening adjustment unit 64a may include the wrist fixing members 63R, 63L and the wrist fixing member fasteners 64R, 64L, and the backhand fastening adjustment unit 67a may include the backhand fixing members 66R, 66L and the backhand fixing member fasteners 67R, 67L.

The first wrist support frames 62R, 62L and the second wrist support frames 65R, 65L may be fixed to the inner side or outer side of the wrists and the back of the hands of the wearer via the wrist fixing members 63R, 63L and the backhand fixing members 66R, 66L. A configuration, structure, and material of the wrist fixing members 63R, 63L and the backhand fixing members 66R, 66L may be equal to or different from those of the waist fixing members 12a, 12b and the thigh fixing members 23R, 23L as described above with reference to FIGS. 1A, 1B, and 1C.

As the wrists and the back of the hands may be fixed to the first wrist support frames 62R, 62L and the second wrist support frames 65R, 65L via the wrist fixing members 63R, 63L and the backhand fixing members 66R, 66L, the wrist joint protectors 60R, 60L may apply a prescribed magnitude of assistance torque to the lower arms and the wrist joints of the wearer. As such, the wrist joint protectors 60R, 60L may assist the wearer in raising or lowering the back of the hands.

In some example embodiments, the wrist fixing member fasteners 64R, 64L and the backhand fixing member fasteners 67R, 67L may provide the wrist fixing members 63R, 63L, the backhand fixing members 66R, 66L, the wrists and the back of the hands of the wearer, the first wrist support frames 62R, 62L, and the second wrist support frames 65R, 65L with fastening force.

When relatively strong shock is applied to the elbows, the wrist fixing member fasteners 64R, 64L and the backhand fixing member fasteners 67R, 67L may cause the wrists and the back of the hands of the wearer to come into close contact with the first wrist support frames 62R, 62L and the second wrist support frames 65R, 65L with strong fastening force, thereby relieving shock to be transmitted to the elbows of the wearer by transmitting the shock to the first wrist support frames 62R, 62L and the second wrist support frames 65R, 65L. When relatively weak shock is transmitted to the elbows, the wrist fixing member fasteners 64R, 64L and the backhand fixing member fasteners 67R, 67L may provide weak fastening force to enhance wearing convenience of the joint protectors 60R, 60L at the wrists and the back of the hands of the wearer.

A configuration, structure, and material of the wrist fixing member fasteners 64R, 64L and the backhand fixing member fasteners 67R, 67L may be equal to or different from the waist fixing member fasteners 13a, 13b and the thigh fixing member fasteners 24R, 24L as described above with reference to FIGS. 1A, 1B, and 1C.

One or more of the first wrist support frames 62R, 62L and one or more of the second wrist support frames 65R, 65L may be physically connected to the wrist joint assistance torque provision units 61R, 61L, and may be rotated in at least one direction by assistance torque provided by the wrist joint assistance torque provision units 61R, 61L. A configuration, structure, and material of the first wrist support frames 62R, 62L and the second wrist support frames 65R, 65L may be equal to or different from those of the first hip support frames 14R, 14L and the second hip support frames 22R, 22L as described above with reference to FIGS. 1A, 1B, and 1C.

The wrist joint assistance torque provision units 61R, 61L may generate various magnitudes of assistance torque in at least one direction. The wrist joint assistance torque provision units 61R, 61L may be set to be driven within a movement range of the wrist joints.

Hereinafter, constituent elements of a fixing member fastener 2 for the joint protection apparatus 1 that provides a human body with fastening force according to one embodiment will be described with reference to FIGS. 3 to 5B.

Figure 3:
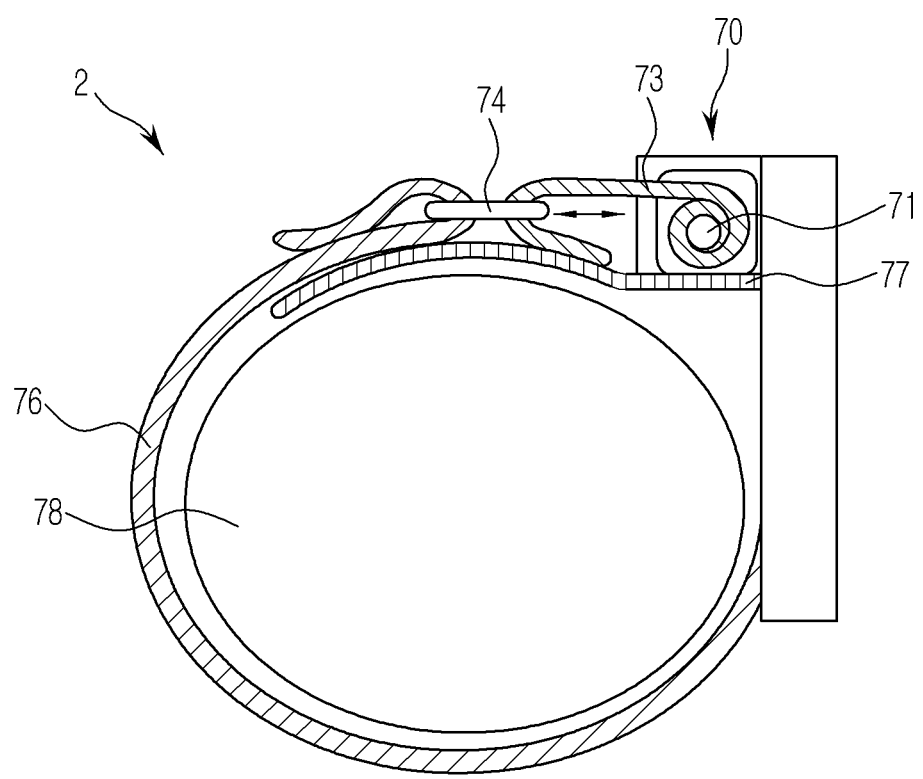
FIG. 3 is a plan view showing a fixing member fastener including a belt and a motor according to some example embodiments.

FIG. 3 shows the fixing member fastener 2 including a belt and a motor according to some example embodiments.

Referring to FIG. 3, the fixing member fastener 2 may include a fastener housing 70, an outer belt 76, an inner belt 73, a belt coupler 74, a motor 71, a fixing frame 77, and a human body seat 78.

The fastener housing 70 may accommodate a variety of elements required to drive the fixing member fastener 2. The fastener housing 70 may accommodate the motor 71 connected to the inner belt 73, and may be connected to the fixing frame 77 and the outer belt 76.

The outer belt 76 may be connected to the fastener housing 70, and transmit fastening force to the human body of the wearer to allow the human body to be fastened to the human body seat 78. The inner belt 73 may be connected to the motor 71 to transmit fastening force provided by the motor 71 to the outer belt 76 through the belt coupler 74. The outer belt 76 and the inner belt 73 may be formed of metal, or may be formed of various elastic materials, such as rubber, etc.

The belt coupler 74 serves to connect the inner belt 73 and the outer belt 76 to each other. The belt coupler 74 may be formed of metal, or may be formed of various elastic members, such as rubber, etc. The belt coupler 74 may have a shape to enable adjustment in the lengths of the inner belt 73 and the outer belt 76, such as a buckle, or may have a shape to disable adjustment in the lengths of the inner belt 73 and the outer belt 76, such as a ring.

The motor 71 may implement winding of the inner belt 73 in response to a control signal of the controller to transmit relatively strong fastening force to the inner belt 73, or may implement unwinding of the inner belt 73 in response to a control signal of the controller to transmit relatively weak fastening force to the inner belt 73. The motor 71 may be a servomotor or a brushless (BL) motor, and may be a DC motor or an AC motor. The motor 71 may have various shapes to transmit fastening force to the inner belt 73.

If the controller sends a control signal to transmit strong fastening force, the motor 71 implements winding of the inner belt 73 in response to the control signal, causing the inner belt 73 to receive fastening force toward the motor 71. Thereby, as the relatively strong fastening force provided to the inner belt 73 is transmitted to the outer belt 76 through the belt coupler 74, the area of the human body seat 78 may be reduced.

Conversely, if the controller sends a control signal to transmit weak fastening force, the motor 71 implements unwinding of the inner belt 73 in response to the control signal, causing the inner belt 73 to receive relatively weak fastening force in a direction opposite to the motor 71. Thereby, as the outer belt 76 is loosened, the area of the human body seat 78 may be increased.

Figure 4A:
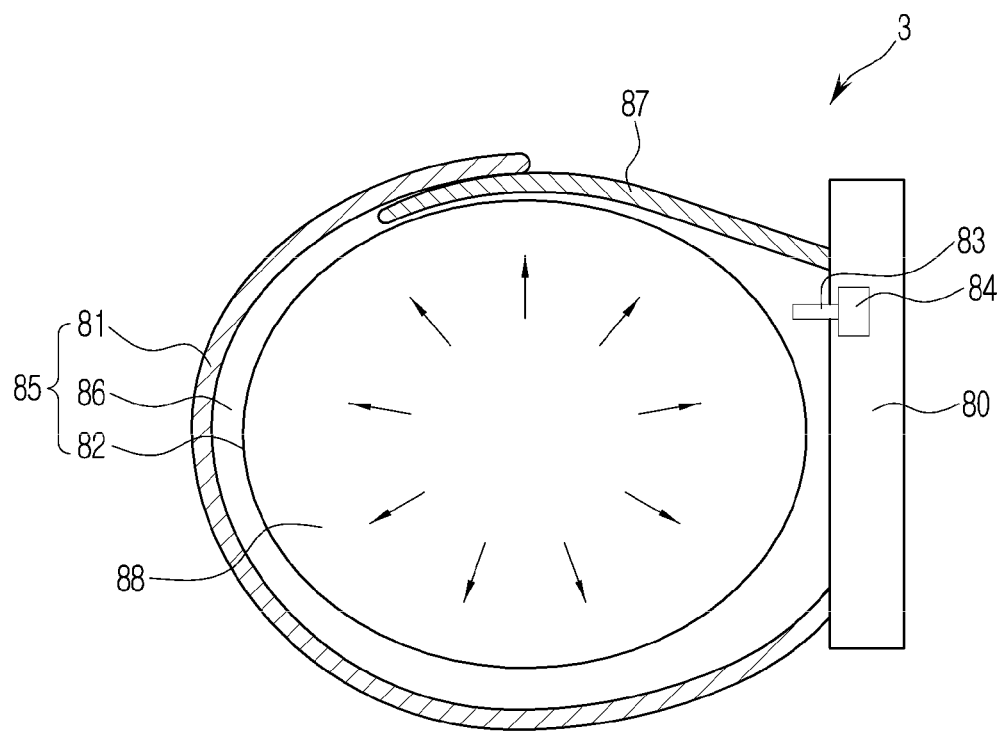
FIG. 4A is a plan view showing provision of weak fastening force by a fixing member fastener including a belt having an air chamber and an actuator according to some example embodiments.
Figure 4B:
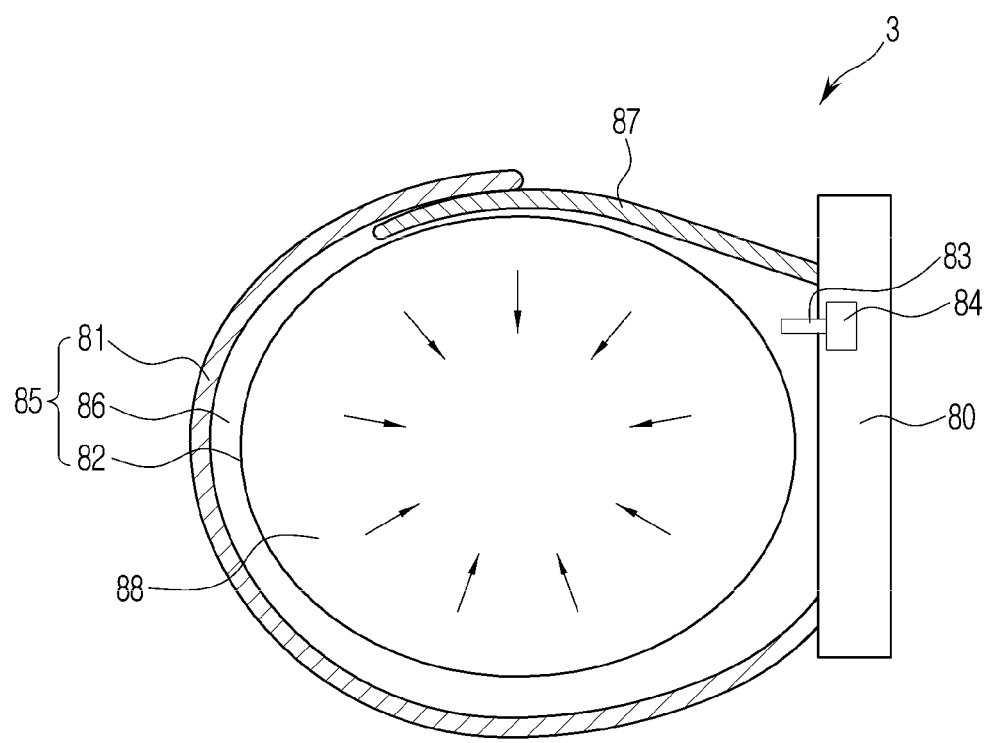
FIG. 4B is a plan view showing provision of strong fastening force by the fixing member fastener including the belt having the air chamber and the actuator according to some example embodiments.

FIGS. 4A and 4B show a fixing member fastener 3 that includes an air chamber 86 defined in the entire belt and an actuator 83 to introduce air into or discharge air from the air chamber 86 for transmission of fastening force according to one embodiment. FIG. 4A shows provision of weak fastening force by the fixing member fastener 3 including the air chamber 86 and the actuator 83, and FIG. 4B shows provision of strong fastening force by the fixing member fastener 3 including the air chamber 86 and the actuator 83.

Referring to FIGS. 4A and 4B, the fixing member fastener 3 may include a fastener housing 80, a belt 85, the actuator 83, an air inlet/outlet port 81, a fixing frame 87, and a human body seat 88.

The fastener housing 80 may accommodate a variety of elements required to drive the fixing member fastener 3. For example, the fastener housing 80 may accommodate the actuator 83 and the air inlet/outlet port 81, and may be connected to the fixing frame 87 and an outer shell 84.

The belt 85 may include the outer shell 84, an inner shell 82, and the air chamber 86. The outer shell 84 may be connected to the fixing frame 87 to prevent leakage of air from the air pouch 86. The inner shell 82 may prevent leakage of air from the air chamber 86 and provide a space for the human body seat 88. The air chamber 86 is defined by the inner shell 82 and the outer shell 84 as walls. The air chamber 86 may provide the human body with fastening force as air is introduced into or discharged from the air chamber 86 based on variation in the hydraulic pressure of the actuator 83. The inner shell 82 and the outer shell 84 may be formed of plastic, or may be formed of various elastic materials, such as rubber, etc.

The actuator 83 may increase hydraulic pressure in response to a control signal of the controller to introduce air into the air chamber 86, thereby transmitting strong fastening force to the belt 85. In addition, the actuator 83 may reduce hydraulic pressure in response to a control signal of the controller to discharge air from the air chamber 86, thereby transmitting weak fastening force to the belt 85. The actuator 83 may have any one exemplarily shape among various shapes to transmit fastening force to the belt 85.

The air inlet/outlet port 84 may function to transfer air into the air chamber 86 as the actuator 83 varies hydraulic pressure to introduce air into or discharge air from the air chamber 86. The air inlet/outlet port 84 may have any one exemplarily shape among various shapes to assist the actuator 83 in introducing air into or discharging air from the air chamber 86. For example, the air inlet/outlet port 84 may be formed of metal or plastic.

If the controller sends a control signal to apply a relatively strong fastening force, the actuator 83 may increase interior hydraulic pressure in response to the control signal, implementing suction of air. As the suctioned air is introduced into the air chamber 86 through the air inlet/outlet port 84, the volume of the air chamber 86 may be increased, and consequently the area of the human body seat 88 may be reduced.

Conversely, if the controller sends a control signal to apply a relatively weak fastening force, the actuator 83 may reduce interior hydraulic pressure in response to the control signal, implementing discharge of air. As the air of the air chamber 86 is discharged through the air inlet/outlet port 84, the volume of the air chamber 86 may be reduced, and consequently the area of the human body seat 88 may be increased.

Figure 5A:
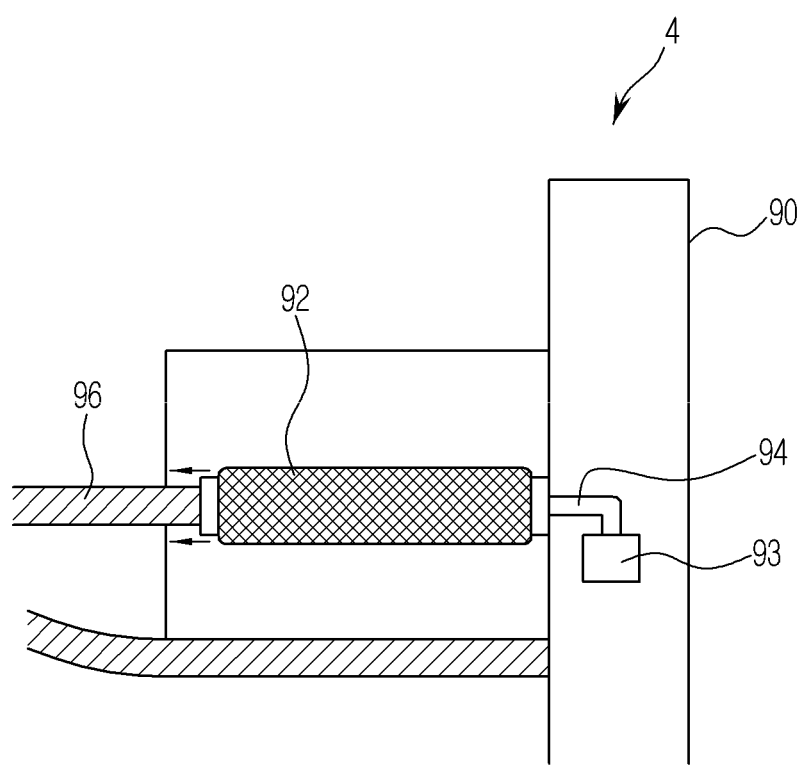
FIG. 5A is a plan view showing provision of weak fastening force by a fixing member fastener including a belt length adjustor in the form of an air chamber and an actuator according to some example embodiments.
Figure 5B:
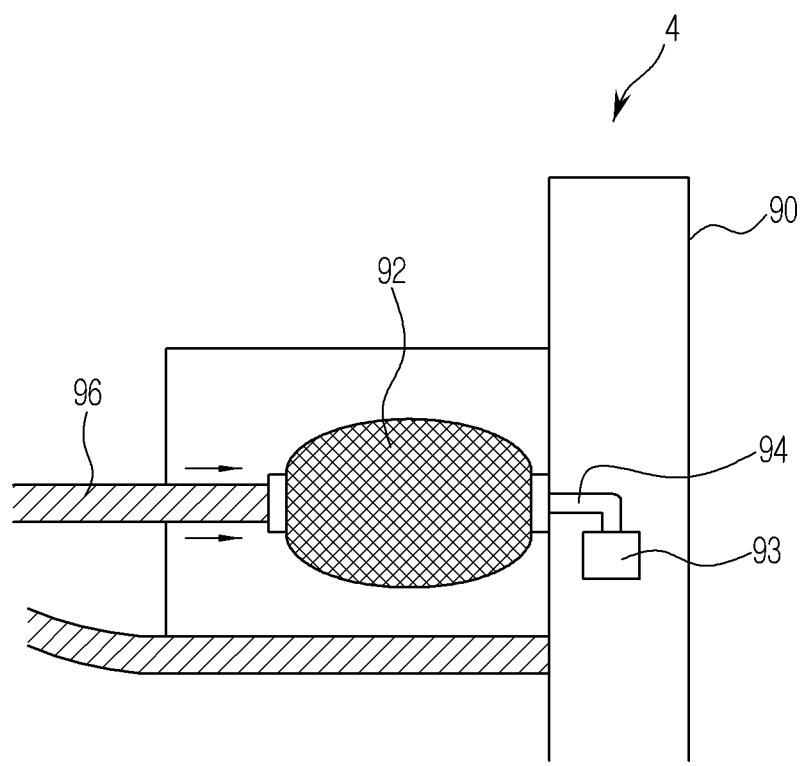
FIG. 5B is a plan view showing provision of strong fastening force by the fixing member fastener including the belt length adjustor in the form of the air chamber and the actuator according to some example embodiments.

FIGS. 5A and 5B show a fixing member fastener 4 that includes a belt length adjustor 92 in the form of an air chamber and an actuator 93 to introduce air into or discharge air from the belt length adjustor 92 for transmission of fastening force according to one embodiment. FIG. 5A shows provision of weak fastening force by the fixing member fastener 4 including the belt length adjustor 92 and the actuator 93, and FIG. 5B shows provision of strong fastening force by the fixing member fastener 4 including the belt length adjustor 92 and the actuator 93.

Referring to FIGS. 5A and 5B, the fixing member fastener 4 may include a fastener housing 90, the belt length adjustor 92, the actuator 93, an air inlet/outlet port 94, and an inner belt 96.

The fastener housing 90 may accommodate a variety of elements required to drive the fixing member fastener 4. For example, the fastener housing 90 may accommodate the actuator 93 to introduce air into or discharge air from the belt length adjustor 92, the air inlet/outlet port 94 to transmit hydraulic pressure to assist introduction/discharge of air by the actuator 93, and the inner belt 96 connected to the belt length adjustor 92.

The belt length adjustor 92 may be an air chamber, the volume of which is increased or reduced via introduction or discharge of air. Through volume increase or reduction, fastening force is horizontally transmitted to the inner belt 96 connected to the belt length adjustor 92. The belt length adjustor 92 may be formed of plastic to prevent leakage of air, or may be formed of various elastic materials, such as rubber, etc., to allow volume increase or reduction.

The actuator 93 may increase hydraulic pressure in response to a control signal of the controller to introduce air into the belt length adjustor 92, thereby transmitting strong fastening force to the inner belt 96. In addition, the actuator 93 may reduce hydraulic pressure in response to a control signal of the controller to discharge air from the belt length adjustor 92, thereby transmitting weak fastening force to the inner belt 96. The actuator 93 may have any one exemplarily shape among various shapes to transmit fastening force to the inner belt 96.

The air inlet/outlet port 94 may function to transfer air into the belt length adjustor 92 as the actuator 93 varies hydraulic pressure to introduce air into or discharge air from the belt length adjustor 92. The air inlet/outlet port 94 may have various shapes to assist the actuator 83 in introducing air into or discharging air from the belt length adjustor 92. For example, the air inlet/outlet port 94 may be formed of metal or plastic.

If the controller sends a control signal to apply a relatively strong fastening force, the actuator 93 may increase interior hydraulic pressure in response to the control signal, implementing suction of air. As the suctioned air is introduced into the belt length adjustor 92 through the air inlet/outlet port 94, the belt length adjustor 92 may be increased in volume and reduced in length, thereby transmitting strong fastening force to the inner belt 96.

Conversely, if the controller sends a control signal to apply a relatively weak fastening force, the actuator 93 may reduce interior hydraulic pressure in response to the control signal, implementing discharge of air. As the air of the belt length adjustor 92 is discharged through the air inlet/outlet port 94, the belt length adjustor 92 may be reduced in volume and increased in length, thereby transmitting weak fastening force to the inner belt 96.

Figure 6A:
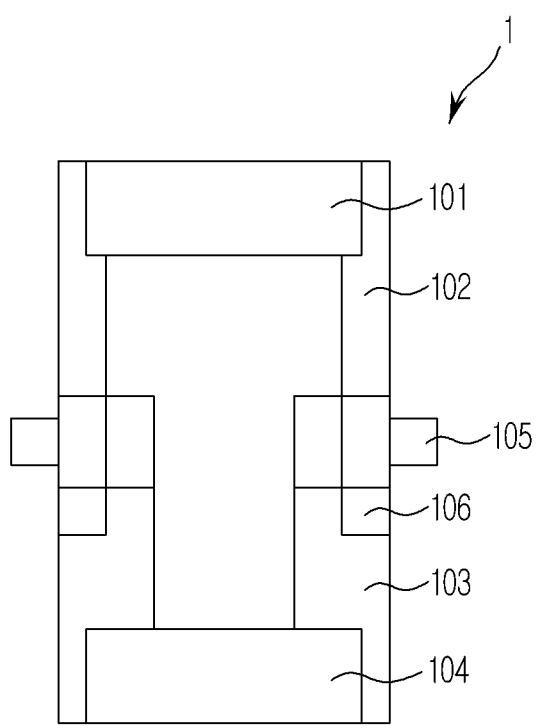
FIG. 6A is a front view of a joint protection apparatus having a guide unit according to some example embodiments.

Hereinafter, constituent elements of a guide unit 106 that prevents first and second support frames 102 and 103 from being rotated beyond a desired (or, alternatively, a predetermined) angle will be described with reference to FIGS. 6A and 6B. FIG. 6A is a front view of the joint protection apparatus having the guide unit 106 according to one embodiment, and FIG. 6B is a side view of the joint protection apparatus having the guide unit 106 according to one embodiment.

Figure 6B:
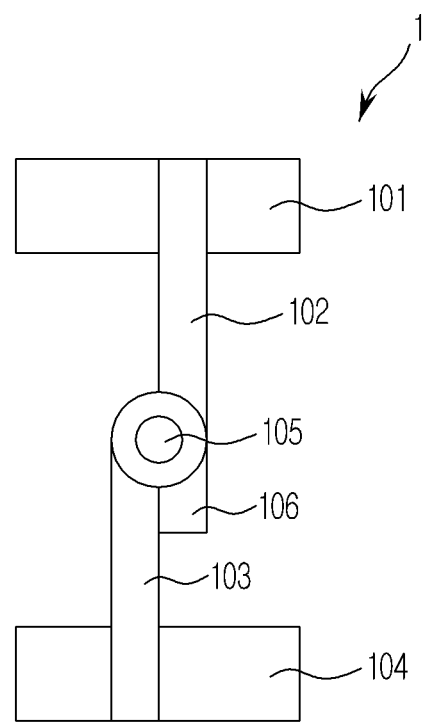
FIG. 6B is a side view of the joint protection apparatus having the guide unit according to some example embodiments.

Referring to FIGS. 6A and 6B, the joint protection apparatus 1 may include a support unit including the first support frame 102, the second support frame 103, and a hinge 105, fastening adjustment units 101 and 104, and the guide unit 106.

Biologically, movement of joints of the wearer above or below a desired (or, alternatively, a predetermined) angle may be undesirable due to muscles or structural reasons, and excessive movement may cause injury, such as dislocation, etc. Therefore, the joint protection apparatus 1 may include the guide unit 106 to prevent movement of joints above or below a desired (or, alternatively, a predetermined) angle.

In some example embodiments, the guide unit 106 may be formed of the same material as or different material from the first support frame 102 and the second support frame 103. In addition, the guide unit 106 may have various shapes to allow the first support frame 102 and the second support frame 103 to be rotatable only within a desired (or, alternatively, a predetermined) angular range. The angular range may vary according to wearing regions.

Hereinafter, a method of dividing a measured angle of a hinge into at least two angular regions and deciding fastening force of each angular region will be described with reference to FIGS. 7 to 9.

Figure 7:
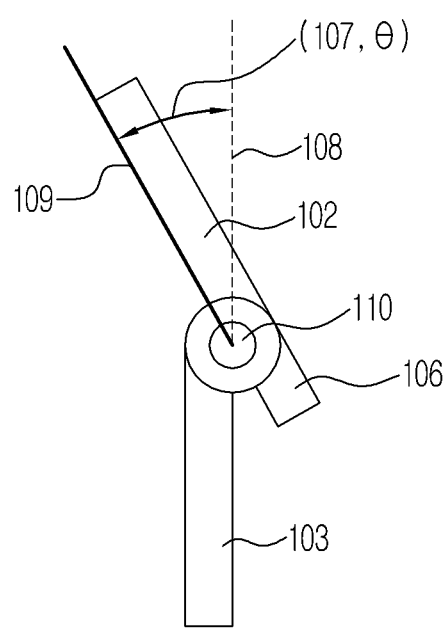
FIG. 7 is a conceptual view showing the angle of a hinge according to one embodiment in which fastening force is adjusted based on the measured angle of a hinge.
Figure 8:
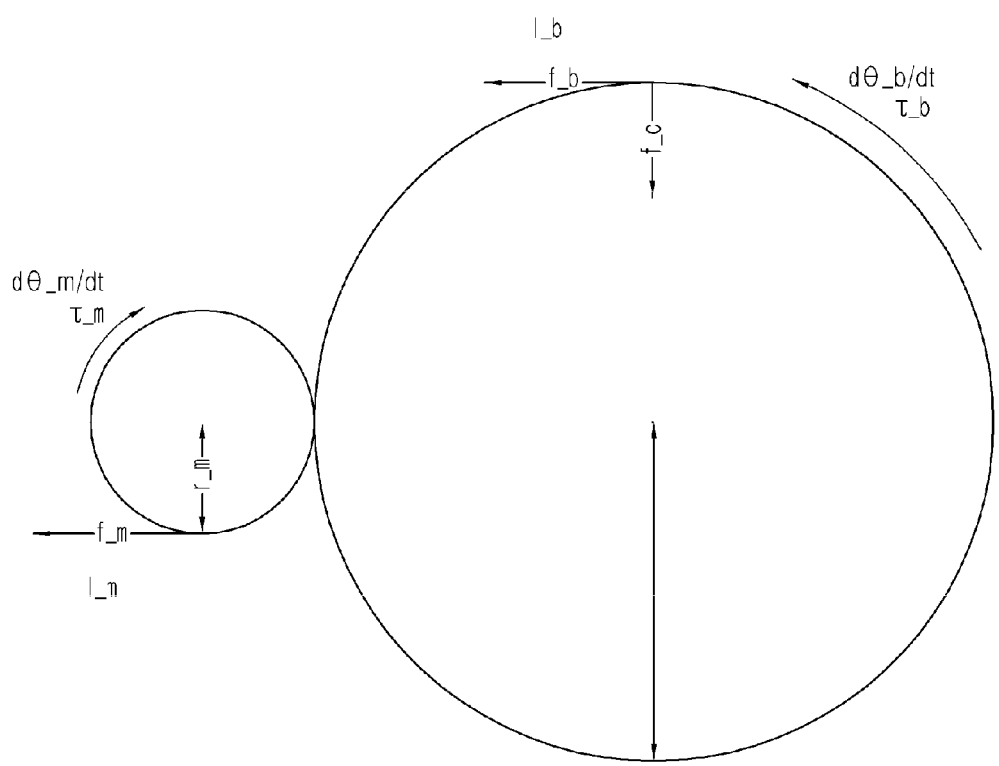
FIG. 8 is a conceptual view showing calculation of fastening force of a fastening adjustment unit including a belt and a motor according to some example embodiments.

FIG. 7 is a conceptual view showing a hinge angle 107 according to some example embodiments, and FIG. 8 is a conceptual view showing calculation of fastening force of a fastening adjustment unit including a belt and a motor according to some example embodiments. In addition, FIG. 9 is a graph showing the magnitude of fastening force 130 with respect to four divided angular regions according to some example embodiments.

Referring to FIG. 7, the angle 107 of a hinge, to which the first support frame 102 and the second support frame 103 are coupled, may vary based on a reference line. The hinge angle 107 may be an angle between a bottom line 109 of the first support frame 102 and an extension line 108 of the second support frame 103.

Referring to FIG. 8, FIG. 8 shows plural variables utilized in equations for calculation of fastening force used by fastening adjustment units including a motor and a belt according to some example embodiments. The plural variables of FIG. 8 will hereinafter be described in the following Equation 1 to Equation 9.

Equation 1 to Equation 9 are equations to calculate belt torque $\tau\_m$ that is fastening force transmitted from a belt to the human body via the relationship between the variables shown in FIG. 8.

$$f\_m = \frac{\tau\_m}{r\_m} \qquad \text{Equation 1}$$

As shown in Equation 1, a tangential force $f\_m$ provided by a motor may be equal to motor torque $\tau\_m$ divided by motor radius $r\_m$.

$$f\_b = \frac{\tau\_b}{r\_b} \qquad \text{Equation 2}$$

As shown in Equation 2, tangential force $f\_b$ transmitted by the motor to the belt may be equal to belt torque $\tau\_b$ divided by belt radius $r\_b$.

$$f\_b = f\_c * r\_b \qquad \text{Equation 3}$$

As shown in Equation 3, the tangential force $f\_b$ transmitted by the motor to the belt may be expressed using Laplace's law, which related to a cylindrical shape to the belt and the wearer's body. Assuming that the belt is a wall of Laplace's law and the wearer's body is fluid of Laplace's law, the tangential force $f\_b$ transmitted by the motor to the belt may be equal to $f\_c$ is centripetal force from a belt surface to the centroid of the belt times the belt radius $r\_b$.

$$f\_c = \frac{f\_b}{r\_b} = \frac{\tau\_m}{r\_m * r\_b} \qquad \text{Equation 4}$$

As shown in Equation 4, the centripetal force $f\_c$ from the belt surface to the centroid of the belt may be expressed using Equation 1 to Equation 3.

When shifting the centripetal force $f\_c$ from the belt surface to the centroid of the belt in Equation 3 to the left side, $f\_c = f\_b/r\_b$ as represented in the left side of Equation 4 may be acquired. Then, by substituting Equation 1 into $f\_b$ of Equation 4 under the assumption that the tangential force provided by the motor $f\_m$ is transmitted to the belt without loss ($f\_m = f\_b$), expression of the right side of Equation 4 may be acquired.

$$m\_d * g * \cos\theta < \mu * f\_c \qquad \text{Equation 5}$$

Equation 5 relates to a condition required to fasten the joint protection apparatus to the wearer's body when weak shock is transmitted to joints of the wearer. In this case, since relatively weak shock is transmitted to joints of the wearer, only gravitational acceleration g related to the weight m_d of the joint protection apparatus may be considered without consideration of impulse.

Among variables of Equation 5, θ is the angle of a hinge, g is acceleration due to gravity, μ is a fixed frictional coefficient between the belt and the wearer's body, and m_d is the weight of the joint protection apparatus.

$$\tau\_m > \frac{r\_m * r\_b * m\_d * g * \cos\theta}{\mu} \qquad \text{Equation 6}$$

Equation 6 relates to a final condition in terms of motor torque τ_m acquired by substituting Equation 4 into Equation 5 that relates to the condition required to fasten the joint protection apparatus to the wearer's body when relatively weak shock is transmitted to joints of the wearer.

When representing in terms of motor torque τ_m by substituting Equation 4 into f_c in Equation 5, fastening force provided by the motor to fasten the joint protection apparatus to the human body may be represented by Equation 6.

$$(m\_d*g+f\_i)*\cos\theta < \mu*f\_c \qquad \text{Equation 7}$$

Equation 7 relates to a condition required to fasten the joint protection apparatus to the wearer's body when relatively strong shock is transmitted to joints of the wearer. In this case, interactive fastening force between the wearer's body and the joint protection apparatus may be calculated in consideration of impulse, f_i transmitted to the wearer's body as well as the gravitational acceleration g of the joint protection apparatus.

$$f\_i = m\_h * g \qquad \text{Equation 8}$$

Equation 8 relates the impulse f_i transmitted to joints of the wearer during walking, the gravitational acceleration g and the weight m_h of the wearer.

$$\tau\_m > \frac{r\_m * r\_b * (m\_d * g + m\_h * g) * \cos\theta}{\mu} \qquad \text{Equation 9}$$

Equation 9 expresses the motor torque τ_m provided by the motor to fasten the joint protection apparatus to the wearer's body by substituting the centripetal force f_c of Equation 4 and the impulse f_i of Equation 8 into Equation 7, where Equation 7 relates to the condition required to fasten the joint protection apparatus to the wearer's body when relatively strong shock is transmitted to joints of the wearer.

Figure 9:
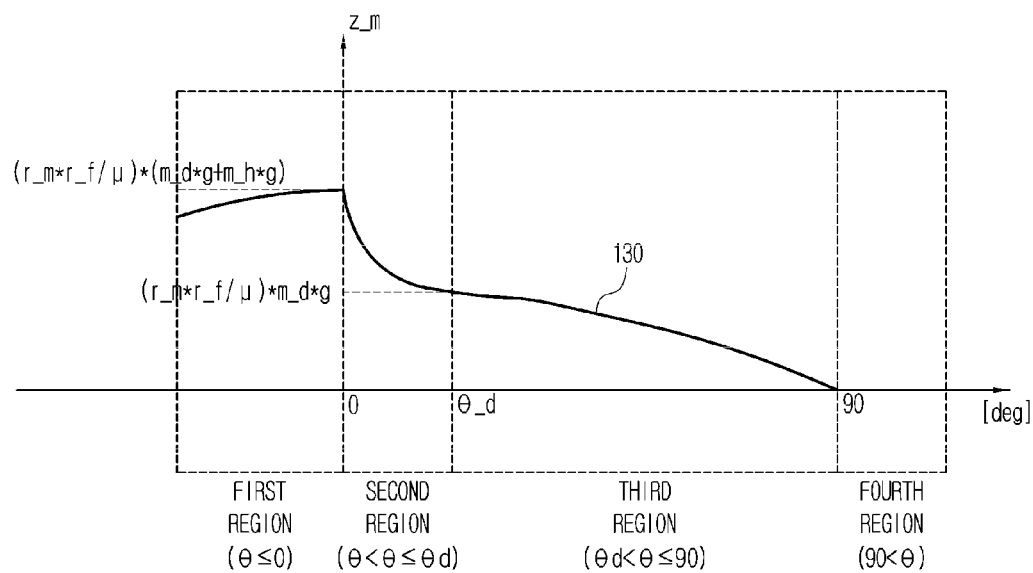
FIG. 9 is a graph showing the magnitude of fastening force with respect to four divided angular regions according to some example embodiments.

FIG. 9 shows a variation of fastening force 130 generated by the motor torque τ_m based on the angle of each angular region under the assumption that the measured angle of a hinge is divided into four angular regions.

For example, torque τ_m 130 provided by the motor in a first region in which the angle of the hinge is zero degrees or less (θ≤0 degrees) may be expressed as the fastening force τ_m=(r_m*r_b*(m_d*g+m_h*g)*cos(θ))/(μ) calculated using Equation 9.

Torque τ_m 130 provided by the motor in a second region in which the angle of the hinge exceeds zero degrees but is a reference angle θ_d or less (0<θ≤θ_d degrees) may be represented as τ_m=((K)/(θ+α))−β (where, K is a gain, and α, β are offset coefficients). The gain K and the reference angle θ_d may be set by the wearer (or alternatively, be predetermined).

Torque τ_m 130 provided by the motor in a third region in which the angle of the hinge exceeds θ_d degrees but is 90 degrees or less (θ_d<θ≤90 degrees) may be expressed as the fastening force τ_m=(r_m*r_b*m_d*g*cos(θ))/(μ) calculated using Equation 6.

In addition, in a fourth region in which the angle of the hinge exceeds 90 degrees (90 degrees<θ), the joint protection apparatus may be fastened even if the motor provides no torque, and thus τ_m may be zero.

As shown in FIG. 9, torque τ_m 130 provided by the motor from the first region to the fourth region is the greatest in the first region in which relatively strong shock is applied to joints of the wearer, and is gradually reduced from the second region to the fourth region because shock applied to joints of the wearer is reduced. Therefore, torque τ_m 130 provided by the motor may be reduced to enhance wearing convenience of the joint protection apparatus.

According to embodiments, the four angular regions as described above in FIG. 9 may be divided into a plurality of angular regions, and thus fastening force τ_m on a per angular region basis may vary.

Hereinafter, the relationship between functions realized by the respective constituent elements of the joint protection apparatus and realization of the functions will be described with reference to FIGS. 10 and 11. FIG. 10 is a block diagram showing decision and provision of fastening force by the support unit, the sensing unit, the controller, and the fastening adjustment unit according to one embodiment, and FIG. 11 is a flowchart showing a process of measuring the angle of a hinge by the sensing unit, dividing the measured angle into four angular regions, and providing the support unit with fastening force corresponding to each angular region.

FIG. 10 shows operations realized by the support unit, the sensing unit, the controller 10, and the fastening adjustment unit and the relationship and sequence of operations.

Referring to FIG. 10, the support unit may include the first support frame 102, the second support frame 103, and a hinge 105, fastening adjustment units 101 and 104, and/or the guide unit 106. The sensing unit may include joint motion sensing units 29, 39, 49, 59 and/or 69. The fastening adjustment unit may include fastening adjustment units 15, 25, 35, 37, 44, 54, 57, 64, and/or 67.

In operation S11, if a hinge of the support unit is rotated via walking motion of the wearer, then in operations S21 and S22, an angle sensor of the corresponding sensing unit may measure variation in the angle of the rotated hinge of the support and transmit the measured variation in the angle of the hinge to the controller. The sensing unit may transmit the measured angle of the hinge via a digital signal having a continuous waveform or a discontinuous form.

In operation S31, the controller may receive the variation in the angle of the hinge transmitted from the sensing unit. In operation S32, the controller may divide the received angle of the hinge into a plurality of set angular regions, where the number of the divided angular regions may be 1 or more. The number of angular regions may vary based on an input value set by the wearer.

In operation S33, the controller may decide fastening force corresponding to the divided angular region. The controller may decide that the fastening force has a fixed value on a per angular region basis, or that the fastening force has a variable value calculated by different equations on a per angular region basis.

For example, the controller may vary the fastening force based on an impulse applied to joints of the wearer. For example, when relatively strong shock is transmitted to joints of the wearer, the controller may calculate fastening force using an equation that considers external force and the weight m_d of the joint protection apparatus 1. For example, the controller 10 may utilize equation 9 to determine the fastening force when relatively strong shock is transmitted to joints of the wearer such that the controller 10 factors in an impulse f_i transmitted to the wearer based on the weight of the wearer Conversely, when relatively weak shock is transmitted to joints of the wearer, the controller may calculate fastening force using an equation that considers only the weight m_d of the joint protection apparatus. For example, the controller 10 may utilize Equation 6 to determine the fastening force when relatively weak shock is transmitted to joints of the wearer such that the controller 10 does not factor the impulse f_i transmitted to the wearer when determining the fastening force.

In operation S41, the fastening adjustment unit may provide the support unit and the human body with the fastening force decided by the controller.

FIG. 11 shows a process of dividing the measured angle of the hinge into angular regions and deciding fastening force in the divided angular regions.

Referring to FIG. 11, in operation S110, the controller may inspect whether a mode of the joint protection apparatus 1 is a variable fastening force mode or an invariable fastening force mode. In operation S145, if the mode of the joint protection apparatus is the invariable fastening force mode, the controller may determine that the fastening force is a fifth fastening force, where the fifth fastening force may be predetermined or set by the wearer.

On the other hand, if the mode of the joint protection apparatus is the variable fastening force mode, in operation S120, the sensing unit may measure an angle θ between respective support frames. In operation S131, the controller may inspect whether or not the measured angle θ is less than or equal to a reference angle θ_d.

If the measured angle θ is less than or equal to the reference angle θ_d, in operation S132, the controller may further inspect whether or not the measured angle θ is less than or equal to zero degrees. If the measured angle θ is less than or equal to zero degrees, in operation S141, the controller may determine that the fastening force is a first fastening force. Alternatively, if the measured angle θ is between zero degrees and a reference angle, in operation S142, the controller may determine that the fastening force is a second fastening force.

If the measured angle θ exceeds the reference angle, in operation S133, the controller may further inspect whether or not the measured angle is less than or equal to 90 degrees. In operation S143, the controller may determine that the fastening force is a third fastening force if the measured angle exceeds the reference angle but is less than or equal to 90 degrees. Alternatively, if the measured angle θ exceeds 90 degrees, in operation S144, the controller may determine that the fastening force is a fourth fastening force degrees.

Thereafter, in operation S150, the fastening adjustment unit may provide the wearer's body and the support unit with one or more of the first fastening force to the fifth fastening force decided by the controller.

In operation S160, the controller may determine if the wearer stops motion by inspecting whether or not the angle between the support frames measured by the sensing unit remains constant. If the angle remains constant, this may indicate that there is no motion of the wearer, and thus, the controller may terminate applying the variable fastening force. If the angle does not remain constant, this may indicate that there is motion of the wearer, and thus the controller may reinspect whether or not the mode of the joint protection apparatus is a variable fastening force mode.

As is apparent from the above description, with a joint protection apparatus and a control method thereof as described above, different magnitudes of fastening force may be provided based on the wearer's motion. In this way, it may be possible to relieve external force applied to joints with a relatively strong fastening force in a motion region in which a relatively strong shock is applied to the joints and to enhance wearing convenience of the joint projection apparatus with a relatively weak fastening force in a motion region in which a relatively less shock is applied to the joints.

The above description is intended to describe technical ideas of the example embodiments, and therefore, those skilled in the art will appreciate that various modifications, additions, and substitutions are possible without departing from the scope and spirit of the disclosure. Accordingly, the example embodiments and the accompanying drawings disclosed herein are intended as examples of the example embodiments, and thus the scope is not limited by the example embodiments and the accompanying drawings. Accordingly, the scope of the example embodiments should be construed by the accompanying claims, and all equivalents.

What is claimed is:

1. A joint protection apparatus comprising:
  a support device, the support device including support frames coupled thereto via a hinge;
  a fastener on the support device, the fastener configured to apply a fastening force to the support device to fasten the support device to a wearer of the joint protection apparatus such that a magnitude of the fastening force varies based on a control signal;
  a sensor configured to measure an angle of the hinge; and
  a controller configured to classify the measured angle into one of a plurality of angle regions, to determine the magnitude of the fastening force based on the classified angle region, and to generate the control signal based on the determined magnitude of the fastening force.

2. The apparatus according to claim 1, wherein the controller is configured to determine the fastening force based on a weight of the wearer of the joint protection apparatus and a weight of the joint protection apparatus.

3. The apparatus according to claim 1, wherein the controller is configured to determine the fastening force such that each of the plurality of motion regions has a fixed fastening force associated therewith.

4. The apparatus according to claim 1, wherein the fastener is configured to apply the fastening force to the support device to fasten the support device to at least one of a hip, knee, ankle, shoulder, elbow, wrist, and waist of the wearer of the joint protection apparatus.

5. The apparatus according to claim 1, wherein the sensor is one of a potentiometer, an absolute encoder, and an incremental encoder.

6. The apparatus according to claim 1, wherein the fastener includes a belt and a motor.

7. The apparatus according to claim 1, wherein the fastener includes an air chamber and an actuator.

8. The apparatus according to claim 1, wherein the controller is configured to determine a assistance torque for the hinge based on the sensed motion, and the joint protection apparatus further comprises:

a driver configured to provide the support device with the assistance torque.

9. A control method of a joint protection apparatus including a support device, the support device including support frames coupled thereto via a hinge, the method comprising:

measuring an angle of the hinge;

classifying the measured angle into one of a plurality of motion regions;

determining a magnitude of a fastening force to apply to the support device based on the classified motion region such that the magnitude of the fastening force varies based on the classified motion region; and applying, via fasteners on the support frames, the fastening force having the determined magnitude to a wearer of the joint protection apparatus.

10. The control method according to claim 9, wherein determining a fastening force includes determining the fastening force based on a weight of the wearer and a weight of the joint protection apparatus.

11. The control method according to claim 9, wherein, in each of the plurality of motion regions, the fastening force has a fixed value associated therewith.

12. The control method according to claim 9, wherein applying the fastening force includes applying the fastening force to fasten the support frames on at least one of the hip, knee, ankle, shoulder, elbow, wrist, and waist of the wearer of the joint protection apparatus.

13. The control method according to claim 9, wherein measuring the angle of the hinge includes measuring the angle of the hinge using one of a potentiometer, an absolute encoder, and an incremental encoder.

14. The control method according to claim 9, wherein the fasteners include a belt and a motor.

15. The control method according to claim 9, wherein the fasteners include an air chamber and an actuator.

16. The control method according to claim 9, further comprising:

determining a assistance torque for the hinge based on the sensed motion; and providing the support frames with the assistance torque using a driver.

* * * * *